United States Patent [19]
Rudolph et al.

[11] Patent Number: 5,721,131
[45] Date of Patent: Feb. 24, 1998

[54] SURFACE MODIFICATION OF POLYMERS WITH SELF-ASSEMBLED MONOLAYERS THAT PROMOTE ADHESION, OUTGROWTH AND DIFFERENTIATION OF BIOLOGICAL CELLS

[75] Inventors: Alan S. Rudolph, Potomac, Md.; Chih-Chang Chu, Ithica, N.Y.; David A. Stenger, Herndon, Va.; Barry J. Spargo, Baltimore, Md.; Jacque Georger, Holden, Mass.

[73] Assignee: United States of America as represented by the Secretary of the Navy, Washington, D.C.

[21] Appl. No.: 234,034

[22] Filed: Apr. 28, 1994

Related U.S. Application Data

[63] Continuation-in-part of Ser. No. 598,194, Oct. 16, 1990, Pat. No. 5,324,591, which is a continuation-in-part of Ser. No. 182,123, Apr. 14, 1988, Pat. No. 5,079,600, which is a continuation-in-part of Ser. No. 22,439, Mar. 6, 1987, Pat. No. 5,077,085.

[51] Int. Cl.$^6$ .................................................. C12N 5/00
[52] U.S. Cl. ................................ 435/240.243; 435/285
[58] Field of Search .......................... 435/240.243, 285

[56] References Cited

U.S. PATENT DOCUMENTS

| | | | |
|---|---|---|---|
| 4,789,601 | 12/1988 | Banes | 428/116 |
| 4,832,759 | 5/1989 | Curtis et al. | 435/285 |
| 5,017,975 | 5/1991 | Ogawa | 357/8 |
| 5,077,085 | 12/1991 | Schnur et al. | 427/98 |
| 5,079,600 | 1/1992 | Schnur et al. | 357/4 |
| 5,108,926 | 4/1992 | Klebe | 435/284 |
| 5,202,227 | 4/1993 | Matsuda et al. | 430/320 |
| 5,324,591 | 6/1994 | Georger, Jr. et al. | 428/552 |

FOREIGN PATENT DOCUMENTS

WO02457 3/1989 WIPO.

OTHER PUBLICATIONS

Ingber et al, J. Cell. Biol. 109: 317–330, 1989.
Stenger et al., Coplanar Moleculor Assemblies of Amino-and Perfluorinated Alkylsilanes: Characterization and Geometric Definition of Mammalian Cell Adhesion & Growth, vol. 114 JACS 8435 3442 (1992).
Kleinfeld et al., Controlled outgrowth of Dissociated Neurous on Patterned Substrates, The Journal of Neuroscience, 8(11): 4098–4120 (Nov. 1988).
Testoff et al., Abstract: Endothelial Cell adhesion and growth on geass and Biodegradable Discs of PGA modified with Self–assembled Monolayers of Aminosilanes, 19th annual Meeting of The Society For Biomaterials, Apr. 28–May 2, 1993.
Testoff et al., Aminoand Perfluorosiland Self–assembled monolayers Promote adhesion and growth of Endothelial Cells: Potential Material Surfaces for Dictating Angiogensis, National Symposium, Orlando, Florida, 15 Nov. 1993.
Amato, L, A NEw Kind of Organic Gardening, Science, vol. 258, p. 1084, 13 Nov. 1992.
Harris, A., Behavior of cultured cells on Substrate of Variable adhesiveness, Experimental Cell Research, vol. 77, pp. 285–297, (1973).
Robinson et al., Morphologic Plasticity and Periodicity: Porcine cerebral Microvascular Cells in Culture, In Vitro. Cell Dev. Biol. 26: 169–180 (Feb. 1990).
Clark et al., Topographical Control of Cell Behaviour. Topography and Cell Behaviour, pp. 439–448 (1986) Development (1986), vol. 99.
Clark et al., Topographical control of Cell Behaviour: II. Multiple Grooved substrate, Development 108: 635–644 (1990).
Torimitsu et al., Selective Growth of Sensory Nerve Fibers on Metal Oxide Pattern in Culture, Developmental Brain Research, 51: 128–131 (1990).
Fields et al., Nerve Regeneration Through Artificial Tubular Implants, Progress in Neurobiology, vol. 33, pp. 87–134, (1989).
Hirono et al., Recognition of Artificial Microstructures by Sensory Nerve Fibers in Culture, Brain Research, vol. 446, pp. 189–194 (1988).
Rohr et al., Patterned Growth of Neonatal Rat Heart Cells in Culture, Circulation Research, vol. 68, No. 1, pp. 114–129 (Jan. 1991).
Ivanova et al., The Use of Phospholipid Film for Shaping Cell Cultures, Nature, vol. 242, pp. 200–201 (Mar. 16, 1973).
Hammarback et al., Neurite Extension Across Regions of Low Cell–Substratum Adhesinty: Implications for the Guidepost Hypothesis of Axonal Pathfinding, Developmental Biology, vol. 117, pp. 655–662 (1986).
Massia et al., Covalent surface Immobilization of Arg–Gly–Asp and Tyr–Ile–Gly–Ser–Arg Containing Peptides to obtain well–defined cell–adhesive substrates, analytical Biochemistry, vol. 187, pp. 292–301 (1990).

(List continued on next page.)

*Primary Examiner*—Michael G. Wityshyn
*Assistant Examiner*—Francisco C. Prats
*Attorney, Agent, or Firm*—Thomas McDonnell; John Karasek

[57] ABSTRACT

A process for forming spatially oriented neo-vascular capillaries comprising: (a) providing a combination ultra-thin film (UTF) pattern of at least one cell adhesion promoter and at least one cell adhesion inhibitor wherein the cell adhesion promoters have a linewidth of between about 50–490 µm; (b) seeding the combination UTF pattern with endothelial cells at an initial seeding cell density; (c) adding a first medium for incubating the seeded endothelial cells until the endothelial cells are grown to confluency; (d) replacing the first medium with a second medium at confluency; and (e) allowing the endothelial cells to differentiate into spatially oriented neo-vascular capillaries.

24 Claims, 10 Drawing Sheets

OTHER PUBLICATIONS

Gross et al., Recording of Spontaneous Activity with Photoetched Microelectrode Surfaces from Mouse Spinal Neurons in culture, Journal of Neuroscience Methods, vol. 5, pp. 13–22, (1982).

Israel et al., An array of Microelectrodes to stimulate and record from cardiac cells in culture, AM. J. Physiol., vol. 247 (Heart Circ. Physiol. 16): H669–H674 (1984).

Regehr, et al., Sealing cultured Invertebrate neurous to embedded Dish Electrodes facilitates long–term stimulation and recording, Journal of Neuroscience Mehtods, vol. 30, pp. 91–106 (1989).

Experimental Cell Research; vol. 103, pp. 436 to 439, (1976).

Science, vol. vol. 246, pp. 245 to 247 (13 Oct. 1989).

Left          Right

SURFACE MODIFICATION OF POLYMERS WITH SELF-ASSEMBLED MONOLAYERS THAT PROMOTE ADHESION, OUTGROWTH AND DIFFERENTIATION OF BIOLOGICAL CELLS

CROSS-REFERENCE TO RELATED APPLICATION

This is a continuation-in-part of prior application with Ser. No. 07/598,194 filed on Oct. 16, 1990, now U.S. Pat. No. 5,324,591, which application is incorporated by reference for all purposes in its entirety, and which is a continuation-in-part of U.S. patent application Ser. No. 07/182,123 filed on Apr. 14, 1988, now U.S. Pat. No. 5,079,600, which application is a continuation-in-part of U.S. patent application Ser. No. 07/022,439 filed on Mar. 6, 1987, now U.S. Pat. No. 5,077,085.

BACKGROUND OF THE INVENTION

1. Field of the Invention

The present invention relates to a method of patterned adhesion, outgrowth and differentiation of biological cells. More particularly, the present invention relates to a method of patterned adhesion, outgrowth and differentiation of endothelial cell to form longitudinally-oriented neo-vascular capillaries.

2. Description of the Related Art

It is well known that the morphological and functional development of adherent types of biological cells is critically dependent in part upon the physical and geometrical properties of the underlying substrate. For the adhesion, outgrowth and differentiation of adherent types of biological cells, substrates which are either unmodified or completely remodified with only a single type of substrate coating have been used almost exclusively.

Often, the ability to influence or monitor intracellular and intercellular processes requires that the adhesive properties be defined with a spatial resolution of extracellular, cellular or subcellular dimensions (i.e. from about 500 µm down to about less than 1 µm). Substrate coating patterns to spatially direct the adhesion, outgrowth and differentiation of biological cells to form tissue repair templates are desired. A method for directing the outgrowth and differentiation of biological cells adhered to suitable substrate coating patterns is also desired.

A variety of substrate patterning techniques were disclosed in the parent application. Use of phospholipid patterns on glass suffer from the instability of phospholipid films. A number of ultra-thin film (UTF) techniques were disclosed in the parent application. For example, silane films anchored to a silicon substrate by chemical and by physical adsorption which may involve siloxane (i.e. Si—O—Si) bridges or Van der Waals forces were discussed in the parent application. Substrates having a terminal ionizable hydroxyl group at the surface can provide anchorage points for silane UTFs. The procedure of using self-assembling monolayer films of silane molecules (SAMs of silane molecules) involves covalent bond formation between the UTF (or SAM) monolayer and the substrate. U.S. Pat. Nos. 5,079,600 and 5,077,085 disclose a method for preparing high resolution patterns of metals on solid substrates. The methods of the two above-identified U.S. patents describe the formation of self-assembling monomolecular films (i.e. UTFs) by chemical adsorption on the surface of the solid substrate, the formation of spatial patterns within the monomolecular films by photolithography and the formation of metal deposition mimicking the photolithographically formed UTF patterns. The U.S. Pat. Nos. 5,079,600 and 5,077,085 are incorporated herein by reference for all purposes in their entirety. While these U.S. patents discuss formation of UTF patterns, there is no suggestion of selective adhesion, outgrowth and differentiation of biological cells.

There is a need for the formation of patterned UTFs of the selective adhesion, outgrowth and differentiation of biological cells such as endothelial cells. There is a need for a method for the adhesion, outgrowth and differentiation of endothelial cells into neo-vascular capillaries. There is a need for a method for the adhesion, outgrowth and differentiation of endothelial cells into longitudinally oriented (i.e. site directed) neo-vascular capillaries.

SUMMARY OF THE INVENTION

It is an object of the present invention to form patterned UTFs suitable for the selective adhesion, outgrowth and differentiation of biological cells such as endothelial cells.

It is another object of the present invention to form patterned UTFs suitable for the selective adhesion, outgrowth and differentiation of endothelial cells into neo-vascular capillaries.

It is another object of the present invention to form UTFs suitable for the selective adhesion, outgrowth and differentiation of endothelial cells into longitudinally oriented neo-vascular capillaries.

It is another object of the present invention to develop a method for the selective adhesion, outgrowth and differentiation of biological cells such as endothelial cells upon UTFs.

It is another object of the present invention to develop a method for the selective adhesion, outgrowth and differentiation of endothelial cells into neo-vascular capillaries upon UTFs.

It is another object of the present invention to develop a method for the selective adhesion, outgrowth and differentiation of endothelial cells into longitudinally oriented neo-vascular capillaries upon UTFs.

These and other objects, which will become apparent in the following detailed description, have been achieved by culturing biological cells such as endothelial cells on a patterned UTF. One surface of the patterned UTF is attached to a substrate. The other surface of the patterned UTF is exposed. One region of the exposed surface of the UTF contains at least one cell adhesion promoter and another region of the exposed UTF surface contains at least one cell adhesion inhibitor. The combination of the cell adhesion promoter(s) and cell adhesion inhibitor(s) forms the UTF pattern upon which the biological cells such as endothelial cells adhere at the exposed surface of the patterned UTF. The pattern of cell adhesion substantially corresponds to the pattern of the cell adhesion promoter(s) within the patterned UTF.

Biological cells (e.g. endothelial cells) are seeded onto the cell adhesion promoter regions of the UTF pattern. After cell adhesion, the outgrowth of the seeded cells is promoted to confluency. Outgrowth to confluency is accomplished by the use of a first medium within which the cells are incubated. After confluency is achieved, the biological cells are caused to differentiate into neo-vascular capillaries upon the patterned UTF. Differentiation after confluency is accomplished by the use of a second medium within which the cells are incubated. It is necessary for the pattern of the cell adhesion promoters and inhibitors to have a pattern wherein linewidths of the cell adhesion promoters is between about 50–490 μm, inclusive. If appropriate pattern linewidths are maintained during adhesion, outgrowth and differentiation, then, upon differentiation, longitudinally oriented neo-vascular capillaries will be formed. However, without the proper linewidths being used in the UTF pattern, without confluency, without the first medium to incubate the cells to confluency, the cells (e.g. endothelial cells) will not differentiate into longitudinally oriented neo-vascular capillaries. Instead, without the proper linewidths, without confluency and without the first medium for incubating the cells to confluency, the cells (e.g. endothelial cells) will differentiate into a tissue mass having little, if any, of the desired spatial orientation found in the longitudinally oriented neo-vascular capillaries.

The patterned UTFs may be produced by a process comprising:

(i) coating a substrate with a compound to obtain an UTF which is reactive to radiation and having an exposed surface of at least one cell adhesion promoter or inhibitor; and (ii) irradiating the UTF in a pattern to obtain an irradiated UTF with a surface region in which at least a fraction of the cell adhesion promoter or cell adhesion inhibitor has been removed.

In another embodiment, the process or forming patterned UTFs may further comprise treating the irradiated UTF with a second compound to bind to the surface region in which at least a fraction of the cell adhesion promoter or cell adhesion inhibitor has been removed.

BRIEF DESCRIPTION OF THE DRAWINGS

In FIG. 3, at the LEFT side and the RIGHT side as marked, the UTF linewidth of the EDA regions was 100 μm and 50 μm, respectively. Note that more complete longitudinally oriented neo-vascular capillary formation along the longitudinal length of the neo-vascular capillary is observed on the RIGHT side as opposed to the LEFT side. The reason for the difference in the growth pattern is that on the LEFT side wherein the linewidth=100 μm, at time=4 days after seeding, the cells had not reached complete confluency while on the RIGHT side wherein the linewidth=50 μm, at time=4 days after seeding, the cells had reached growth to confluency. Thus, for the cells growing on the LEFT side, the b-FGF was added too early while, for the cells growing on he RIGHT side, the b-FGF was added at the time when confluency was reached. Clearly, the time to confluency is shorter for a narrower linewidth. The cells are labeled as sample MT910 for convenience.

In FIG. 5a, the metalized surface of a fused silica photolithographic mask was tightly positioned against an EDA coated glass microscope slide. The photochemical modification of the EDA coated glass slide with a 15 J/cm$^2$ deep ultraviolet (DUV) exposure through the photolithographic mask resulted in the formation of the slide as shown in FIG. 5b. Note that wherever the EDA was unprotected by the photolithographic mask during DIN exposure, the EDA was removed (i.e. photo-ablated) leaving behind hydroxyl groups exposed on the surface of the glass. The DUV exposure resulted in the formation of a UTF pattern corresponding to the dimensions of the photolithographic mask wherein, during DUV irradiation, exposed portions of the EDA regions were modified to exposed hydroxyl groups on the underlying glass slide surface and the unexposed regions of EDA remained intact with exposed amine (i.e. —$NH_2$) groups. The 15 J/$cm^2$ DUV exposure resulted in the photochemical modification of the EDA region that was unshielded/unmasked from the DUV radiation to produce a pattern of oxidized surface molecules which are collectively represented as hydroxyl groups on the glass surface. Immediately following DUV irradiation, the glass slide as depicted in FIG. 5b, was bathed with a 1% mixture (i.e. solution) of 13F in toluene to selectively remodify the previously exposed hydroxyl regions, producing the orthogonal EDA/13F UTF as depicted in FIG. 5c.

FIGS. 12 and 13) were taken at confluency. In both FIGS. 12 and 13, the photographs were taken 48–72 hours post seeding at confluence. In both FIGS. 12 and 13, the initial HUVEC seeding cell density was 2,500 cells/$cm^2$. The linewidth in FIG. 12 was 50 μm and the linewidth in FIG. 13 was 50 μm. In both FIGS. 12 and 13, the cells were grown in a first medium known as M-199 containing up to 2% (v/v) fetal bovine serum, 10 ng/ml endothelial cell growth factor (ECGF) and bovine brain extract (BBE) among other components. The growth medium (i.e. first medium) was replaced every other day with fresh medium (i.e. fresh first medium). FIG. 12 demonstrates that at linewidth=50 μm the desired longitudinal orientation is achieved at confluency. FIG. 13 demonstrates that at linewidth=500 μm the desired longitudinal orientation is lacking at confluency.

In FIG. 15, various spatially oriented paths suitable for use with the currently disclosed invention are schematically drawn wherein spatially oriented endothelial neo-vascular capillaries are formed on the path of the cell adhesion promoters having a linewidth as defined within this patent application, infra. The spatial orientations shown in FIG. 15 are merely illustrative of a few of the thousands of possible spatial orientations of cell adhesion promoters. Spatially orientated neo-vascular capillary formation includes longitudinally oriented neo-vascular capillary formation as well tangentially oriented neo-vascular capillary formation wherein the neo-vascular capillaries form tangentially along whatever pattern is defined by the cell adhesion promoter region as exemplified in FIG. 15.

DESCRIPTION OF THE PREFERRED EMBODIMENTS

The following detailed description of the invention is provided to aid those skilled in the art in practicing the present invention. However, the following detailed description of the invention should not be construed to unduly limit the present invention. Variations and modifications in the embodiments discussed may be made by those of ordinary skill in the art without departing from the scope of the present inventive discovery.

Several terms are used in this application which have meaning as described below. "Ultra-thin films" or UTFs refer to films or layers which are at least one molecule thick. Often, the films used are thinner than about one quarter of the wavelength of light used to expose the substrate, and may be as thin as a monomolecular layer. "EDA" refers to an exemplary aminosilane cell adhesion promoter which has the name N-2-aminoethyl-3-aminopropyl-trimethoxysilane. "13F" refers to an exemplary perfluorinated alkylsilane cell adhesion inhibitor which has the name (tridecafluoro-1,1,2, 2-tetrahydrooctyl)-1-dimethylchlorosilane. "SAM" refers to a self-assembled monolayer which is alternatively referred to as the ultra-thin film (UTF). "HUVEC" refers to human umbilical vein endothelial cell which is one embodiment of an endothelial cell type used in the formation of longitudinally oriented neo-vascular capillaries. "PCMVEC" refers to porcine cerebral microvascular endothelial cell which is another embodiment of an endothelial cell type used in the formation of longitudinally oriented neo-vascular capillaries. "b-FGF" refers to basic fibroblast growth factor which is used to cause differentiation of the seeded endothelial cells on the substrate. "ECGF" refers generically to endothelial cell growth factor. "BBE" refers to bovine brain extract. The term "linewidth" refers to the width along a region of the substrate coated with for example EDA. The linewidth is the width of the region of the UTF comprised of cell adhesion promoters such as the exemplary EDA molecules attached to the substrate. The term "substrate" refers to the underlying material on which the UTF is coated. The term "confluency" refers to the condition when the seeded endothelial cells on the UTF have grown to cover nearly completely the full linewidth of the cell adhesion promoters such as the exemplary EDA coated portion forming a single planar mass of endothelial cells.

Figure 1:
FIG. 1 is a photograph of endothelial cells that were adhered, grown and photographed 4 days after seeding. The cells were seeded onto a patterned UTF attached to a glass substrate. The initial endothelial seeding cell density at time=0 hours was 10,000 cells/cm$^2$. No basic fibroblast growth factor (b-FGF) was added. Therefore, no differentiation into neo-vascular capillaries is seen. The linewidth of the N-2-aminoethyl-3-aminopropyl-trimethoxysilane (EDA) region upon which the cells were seeded was 500 μm. Due to the large linewidth, no longitudinal orientation at confluency is observed. The cells were grown in a first medium known as M-199 containing up to 2% (v/v) fetal bovine serum, 10 ng/ml endothelial cell growth factor (ECGF) and bovine brain extract (BBE) among other components. The growth medium (i.e. first medium) was replaced every other day with fresh medium (i.e. fresh first medium). The cells were labelled as sample MT411 for convenience.
Figure 2:
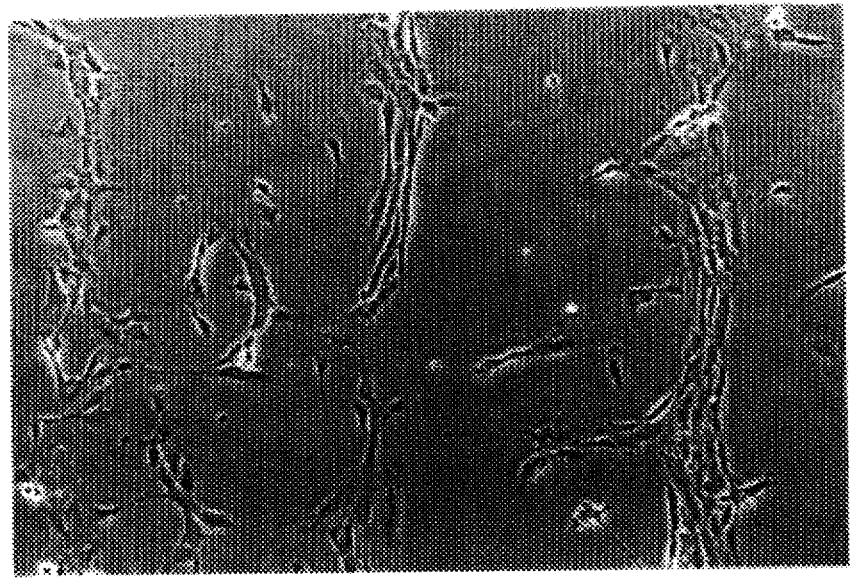
FIG. 2 is a photograph of endothelial cells that were adhered, grown and photographed 5 days after seeding. The cells were seeded onto a patterned UTF attached to a glass substrate. The initial endothelial seeding cell density at time=0 hours was 10,000 cells/cm$^2$. The linewidth of the EDA region upon which the cells were seeded was 50 μm. Basic fibroblast growth factor was added at time=4 days after seeding to promote cell differentiation at a concentration of 5 ng/ml. However, cell differentiation into longitudinally oriented neo-vascular capillaries is NOT obtained. The lack of the longitudinal orientation is due to the late addition of the basic fibroblast growth factor at a time after confluency and when overgrowth had already been reached. This figure illustrates the importance of adding the b-FGF at the precise time when confluency is reached. The cells were first grown in a first medium known as M-199 containing up to 2% (v/v) fetal bovine serum, 10 ng/ml endothelial cell growth factor (ECGF) and bovine brain extract (BBE) among other components. At time=4 days when b-FGF was added, the cells were incubated in a second medium known as M-199 containing up to 2% (v/v) fetal bovine serum and b-FGF at a concentration of 5 ng/ml among other constituents. The incubation medium (i.e. second medium) was replaced every other day with fresh incubating medium (i.e. second medium). Note, however, that upon the addition of b-FGF, the ECGF and BBE must be removed. The presence of ECGF and BBE interferes with the differentiation process promoted by the b-FGF. The cells were labelled as sample MT721 for convenience.
Figure 3:
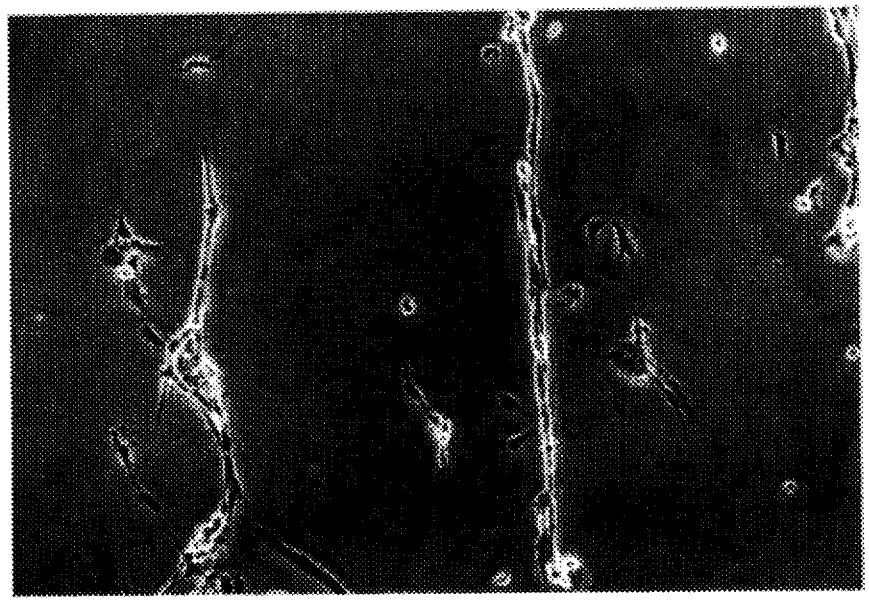
FIG. 3 is a photograph of endothelial cells that were adhered, grown, differentiated and photographed 6 days after seeding. The cells were seeded onto a patterned UTF attached to a glass substrate. The initial endothelial seeding cell density at time=0 days was 2,500 cells/cm$^2$. B-FGF was added at time=4 days after seeding to promote cell differentiation at a concentration of 5 ng/ml.
Figure 8:
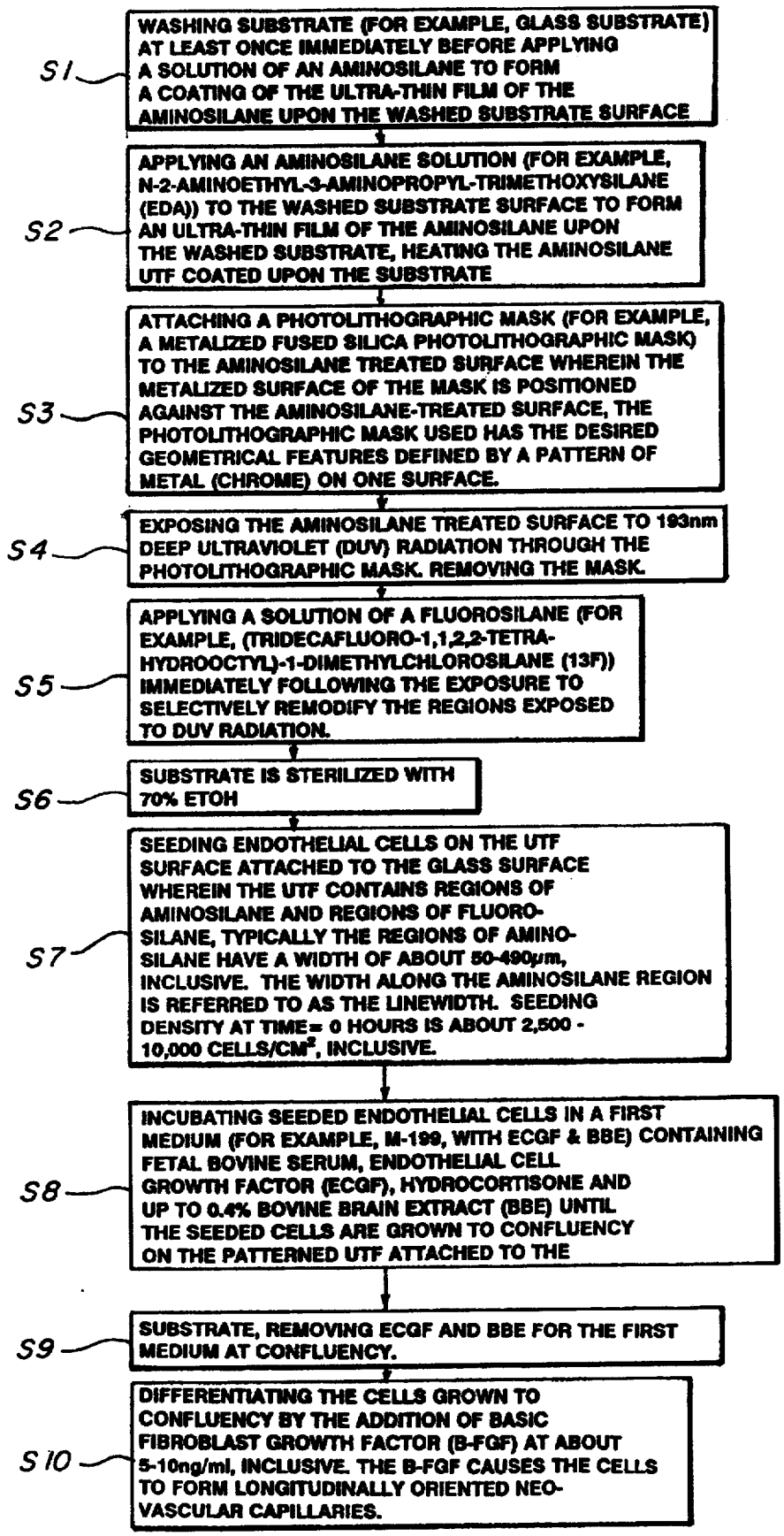
FIG. 8 is a flow chart showing the steps involved in the longitudinally oriented neo-vascular capillary formation process according to one embodiment of the present invention.
Figure 9:
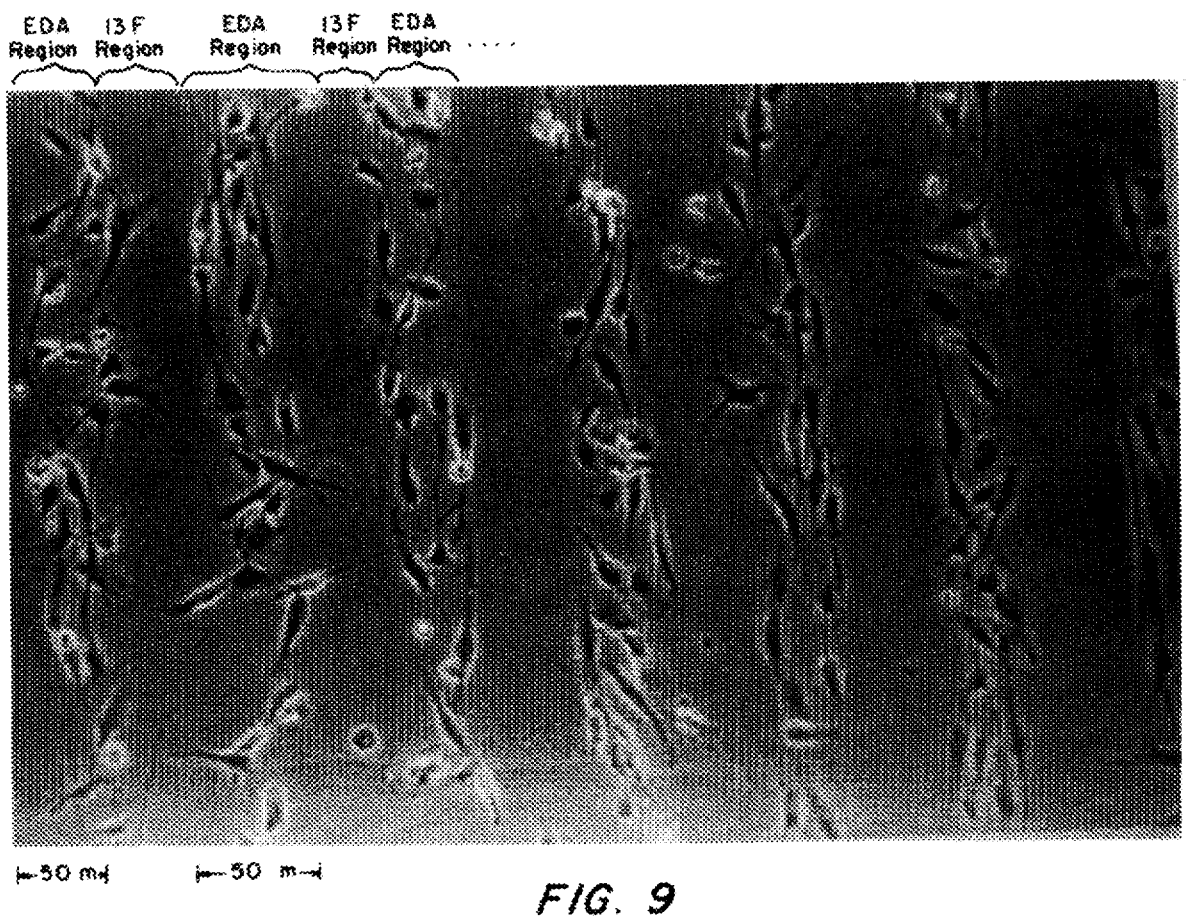
FIG. 9 is a photograph taken 4 hours after seeding a EDA/13F patterned UTF upon a glass substrate. The initial endothelial seeding cell density was 2,500 cells/$cm^2$ at time=0 hours. The linewidth of the exemplary EDA regions was 50 μm. The cells were grown in a first medium known as M-199 containing up to 2% (v/v) fetal bovine serum, 10 ng/ml endothelial cell growth factor (ECGF) and bovine brain extract (BBE) among other components. The growth medium (i.e. first medium) was replaced every other day with fresh medium (i.e. fresh first medium). The photograph demonstrates the selective adhesion of exemplary endothelial cells on the exemplary EDA regions and also demonstrates a preference of adhesion of the exemplary endothelial cells to the exemplary EDA regions over the exemplary 13F regions.
Figure 10:
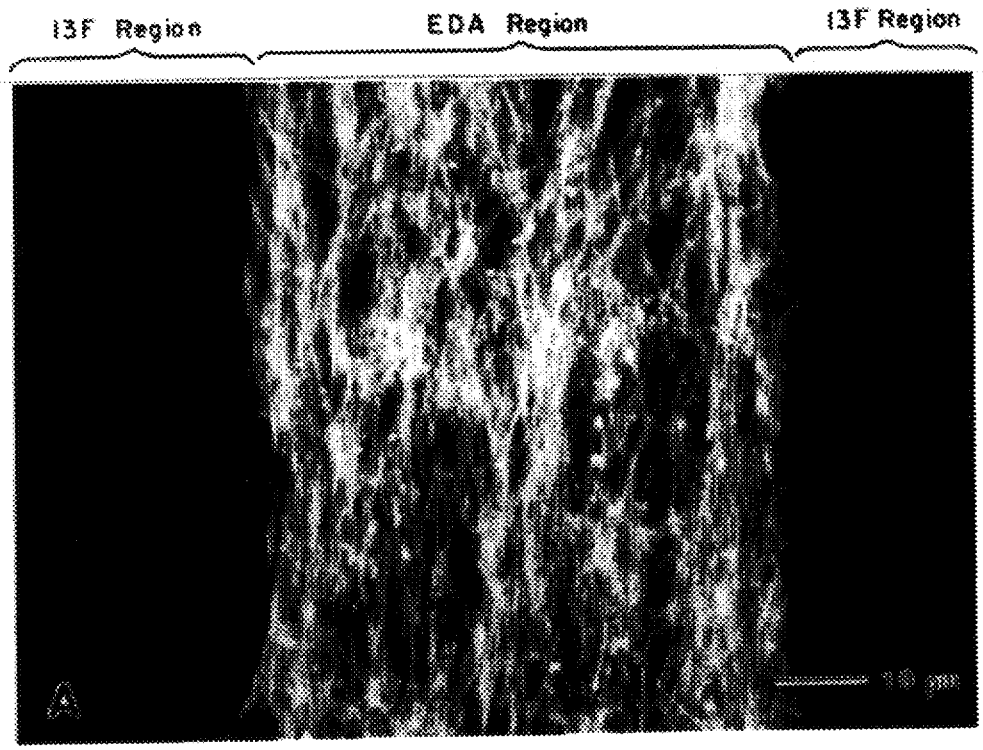
FIGS. 10 (panel A) and 11 (panel B) are both photographs taken of Human Umbilical Vein Endothelial Cells (HUVECs) stained with phalloidin fluorescent stain for cytoskeleton. In both FIGS. 10 and 11, the photographs were taken 48–72 hours post seeding at confluence. In both FIGS. 10 and 11, the initial HUVEC seeding cell density was 2,500 cells/$cm^2$. In both FIGS. 10 and 11, the linewidth of the EDA region was 50 μm. In both FIGS. 10 and 11, the cells were grown in a first medium known as M-199 containing up to 2% (v/v) fetal bovine serum, 10 ng/ml endothelial cell growth factor (ECGF) and bovine brain extract (BBE) among other components. The growth medium (i.e. first medium) was replaced every other day with fresh medium (i.e. fresh first medium). The photograph demonstrates the selective adhesion of exemplary endothelial cells on the exemplary EDA regions and also demonstrates a preference of adhesion of the exemplary endothelial cells to the exemplary EDA regions over the exemplary 13F regions. Note that in FIG. 10 (panel A), the photograph demonstrates the longitudinal orientation of cells on EDA at confluence. Note that in FIG. 11 (panel B), the arrow in panel B is directed to a cell attempting to adhere to the 13F region of the patterned UTF (i.e. pattern of EDA/13F). Note the squamous appearance of the cell in the 13F region at the arrow in FIG. 11. Also note the lack of elongation of the cell on the exemplary 13F region and the poor adhesion on the 13F region at the arrow, as indicated, in FIG. 11.
Figure 11:
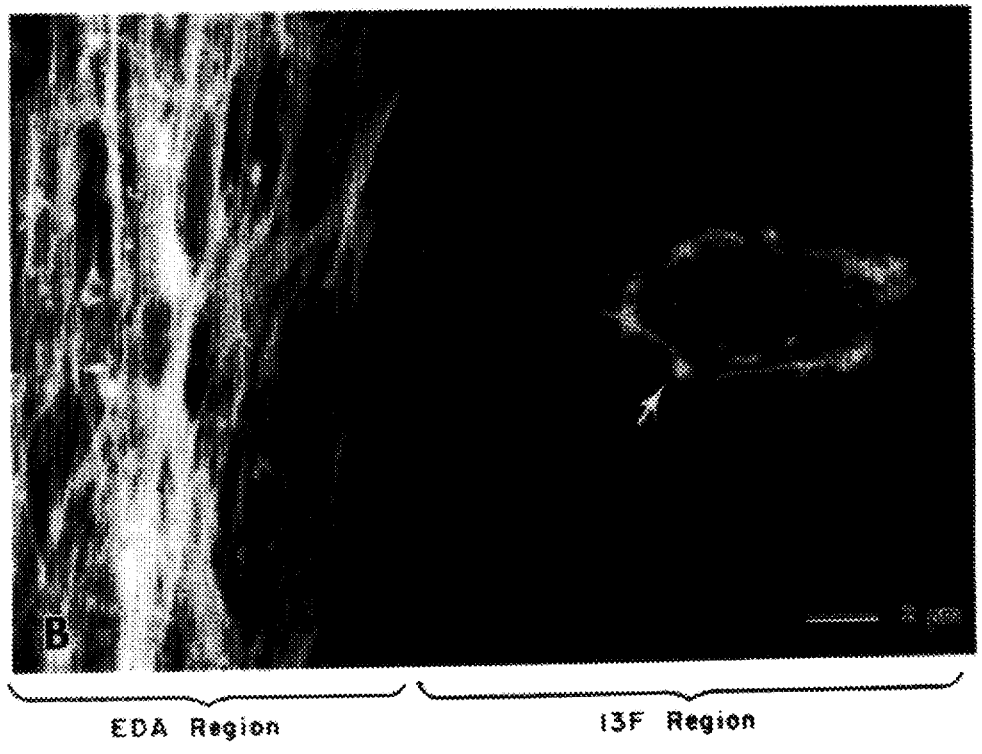
Figure 12:
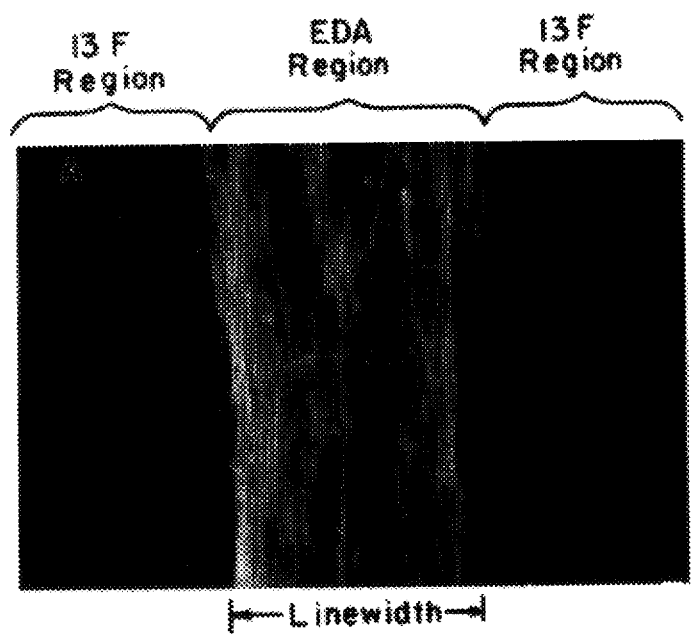
FIGS. 12 (panel A) and 13 (panel C) are both photographs taken of Human Umbilical Vein Endothelial Cells (HUVECs) stained with phalloidin fluorescent stain for cytoskeleton. Both photographs (i.e.
Figure 13:
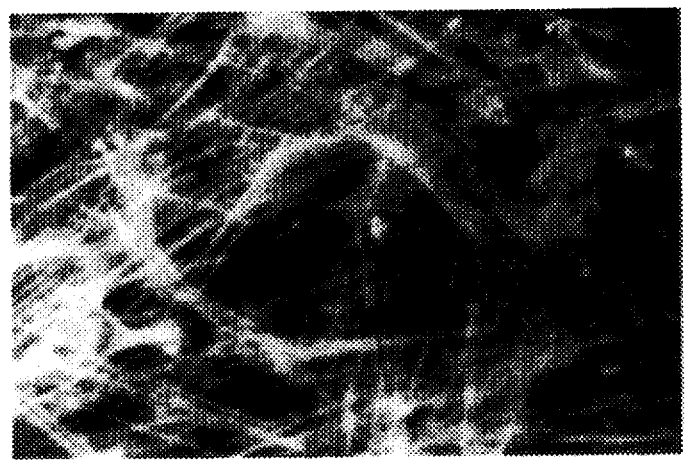
Figure 14:
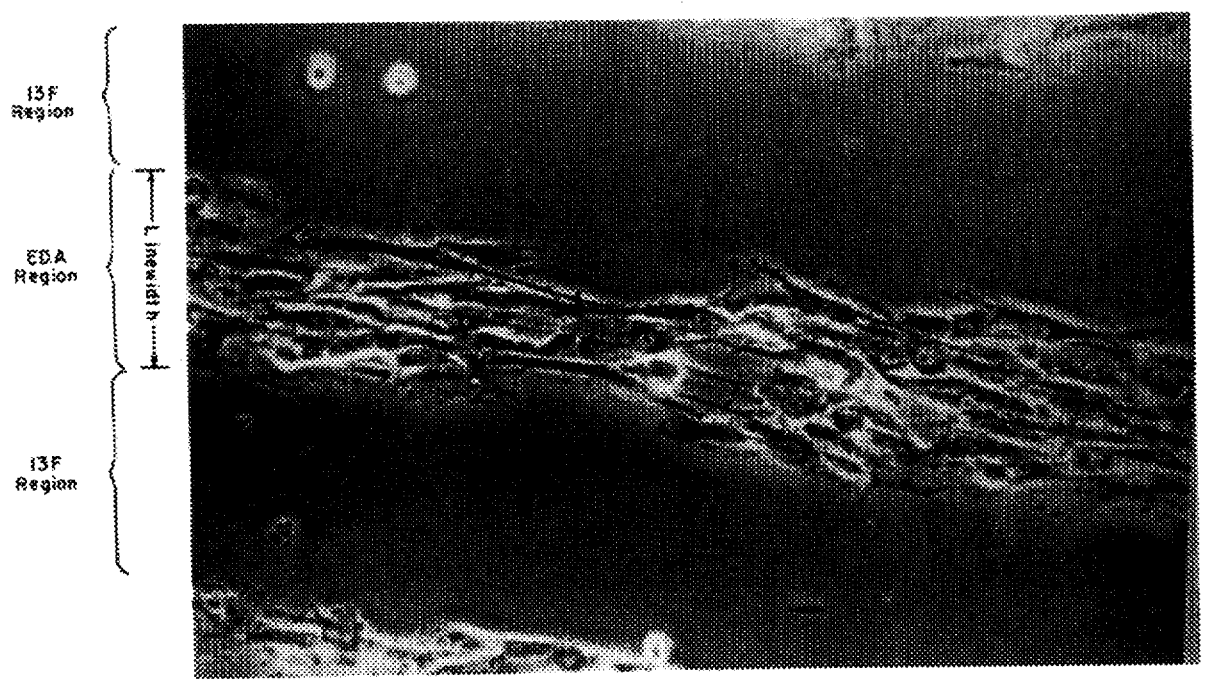
FIG. 14 is a photograph taken at 48–72 hours after seeding a EDA/13F patterned UTF upon a glass substrate. The initial endothelial seeding cell density was 2,500 cells/$cm^2$ at time=0 hours. The linewidth of the EDA regions is 50 μm. The cells were grown in a first medium known as M-199 containing up to 2% (v/v) fetal bovine serum, 10 ng/ml endothelial cell growth factor (ECGF) and bovine brain extract (BBE) among other components. The growth medium (i.e. first medium) was replaced every other day with fresh medium (i.e. fresh first medium). The photograph demonstrates the selective adhesion of exemplary endothelial cells on the EDA regions and also demonstrates a preference of adhesion of the exemplary endothelial cells to the EDA regions over the 13F regions. The photograph depicts the cells at confluency and further depicts the longitudinal orientation of the cells at confluency. The photograph also depicts the maintenance of selective adhesion on EDA regions even at confluency. Lastly, the photograph demonstrates the maintenance of the inhibition of cell adhesion on 13F regions even at confluency.
Figure 15:
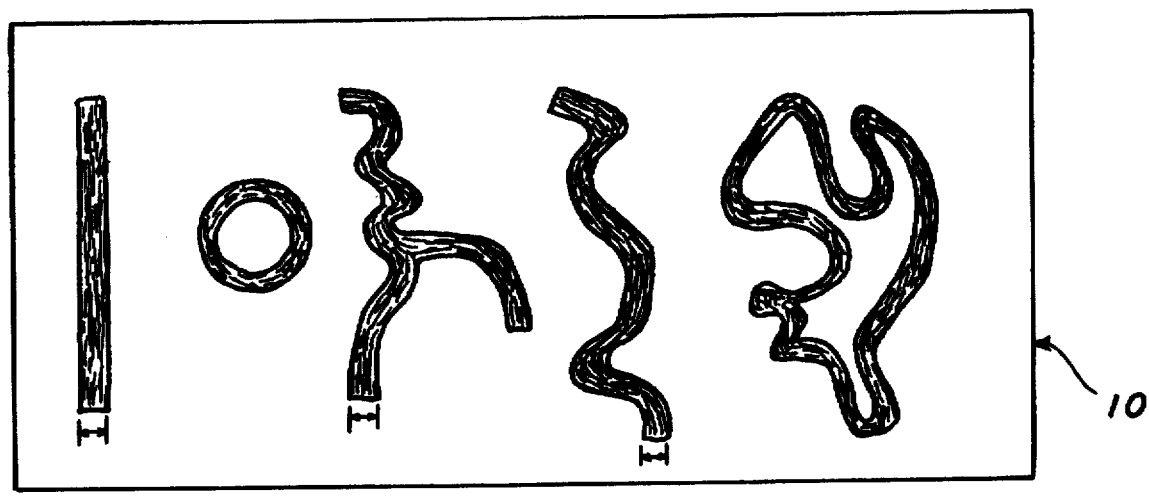
FIG. 15 is a schematic drawing of exemplary spatial orientation of cell adhesion promoters deposited on a substrate 10 upon which endothelial cells can be adhered, grown and differentiated to form site directed or longitudinally oriented neo-vascular capillaries. Note that the endothelial cells adhere to, grow and differentiate on a path parallel to the pattern of the cell adhesion promoters. The spatial orientation of the cell adhesion promoters can be a straight line, a circle, a curved or irregularly shaped line, a closed loop, or an irregularly shaped closed loop. The endothelial cell are adhered to, grown on and differentiated into neo-vascular capillaries along the pattern or path of the of the cell adhesion promoters.

Referring to FIG. 8, the steps involved in the formation of longitudinally oriented neo-vascular capillaries are outlined. The term "longitudinally oriented" refers to the aligned orientation of the neo-vascular capillaries formed along the longitudinal axis of each of the individual capillaries as is depicted on the right side as shown in FIG. 3.

Beginning with $S_1$, the process for the formation of longitudinally oriented neo-vascular capillaries comprises the steps of:

(a) washing a substrate at least once with a washing solution;

(b) applying an aminosilane cell adhesion promoting solution to the washed substrate to form a self-assembled monolayer of the aminosilane on the substrate forming an ultra-thin film of the aminosilane upon the washed substrate;

(c) heating the aminosilane coated substrate;

(d) positioning a metalized photolithographic mask upon the aminosilane coated ultra-thin film formed on the substrate, the mask having gaps within the mask wherein the width of the mask between the gaps is between about 50 to 490 μm, inclusive;

(e) exposing the aminosilane exposed within the gaps of the photolithographic mask to deep ultraviolet (DUV) wavelength radiation to selectively remove the aminosilane exposed to the DUV light;

(f) removing the mask;

(g) applying a solution of a perfluorinated alkylsilane to the DUV exposed UTF attached to the substrate to remodify the regions exposed to the DUV radiation;

(h) seeding the UTF with endothelial cells at a seeding density of about 2,500–10,000 cells/cm$^2$ after applying the perfluorinated alkylsilane solution to the DUV exposed regions;

(i) adding a first medium for incubating the seeded endothelial cells until the seeded cells are grown to confluency;

(j) replacing the first medium with a second medium;

(k) adding a growth factor at a concentration of about 5–10 ng/ml to cause differentiation of the confluent cells to form longitudinally oriented neo-vascular capillaries; and (l) allowing the cells from step (i) to differentiate into longitudinally oriented neo-vascular capillaries.

Note that the above outlined exemplary process indicates in step (b) that an aminosilane is first deposited onto the washed substrate and that in step (g) a perfluorinated alkylsilane is deposited in the DUV exposed regions. It is entirely possible to first deposit a perfluorinated alkylsilane in step (b) and later deposit an aminosilane in step (g) in the DUV or other suitable wavelength radiation exposed regions.

Figure 5A:
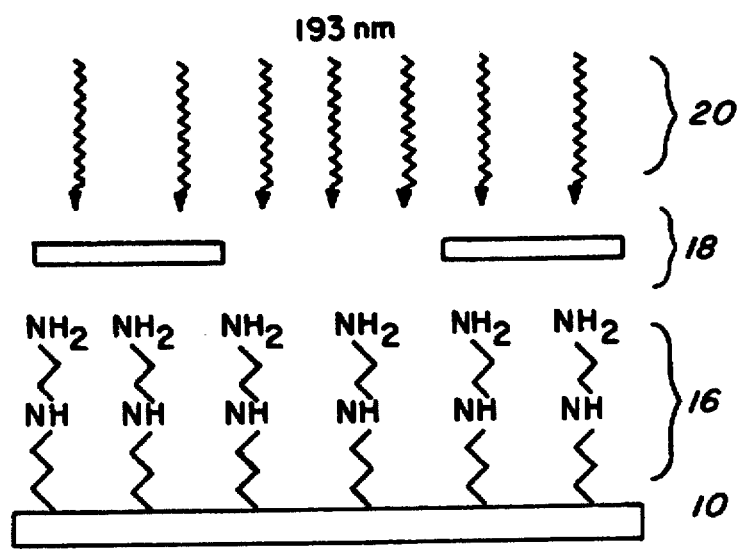
FIGS. 5a, 5b and 5c illustrate schematically the procedure for the preparation of a patterned {N-2-aminoethyl-3-aminopropyl-trimethoxysilane (EDA)/(tridecafluoro-1,1,2,2,-tetrahydrooctyl)-1-dimethylchlorosilane (13F)} ultra-thin film onto a glass substrate.
Figure 5B:
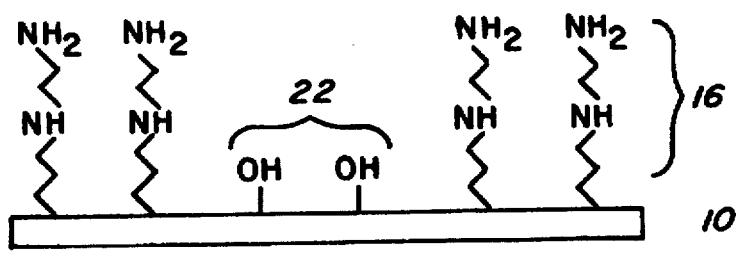
Figure 5C:
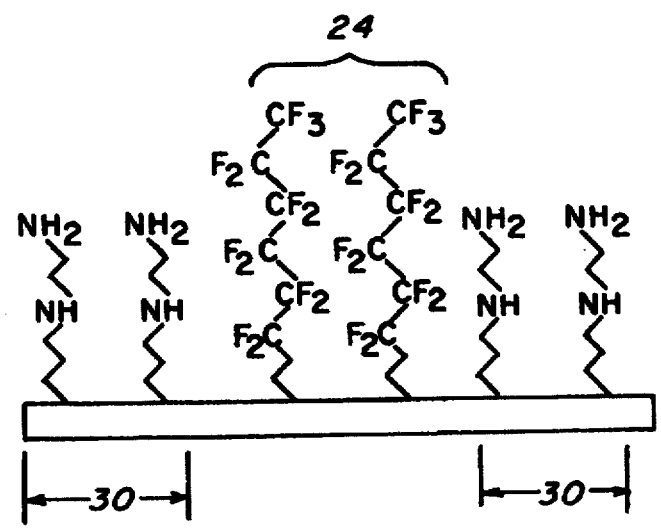

A preferred embodiment of the present process is shown in FIGS. 5a, 5b and 5c. FIG. 5a illustrates the irradiation, through a mask, of a substrate which has been coated with a cell adhesion promoter to form an UTF which has an exposed surface of —NH$_2$CH$_2$CH$_2$NH$_2$ groups. After irradiation, a region which is devoid of cell adhesion promoter is formed as shown in FIG. 5b. The process may then be continued by treating the surface of the substrate as shown in FIG. 5b with a reagent to bind to the exposed region with a cell adhesion inhibitor as shown in FIG. 5c. Of course, it is to be understood that the present process does not require that the cell adhesion promoter be coated first. Thus, the process depicted in FIGS. 5a, 5b and 5c may be varied to include a process in which the substrate is first coated with a radiation reactive cell adhesion inhibitor, then the coated surface is irradiated to form a reactive region and the surface is treated with a second compound to remodify the reactive region with a cell adhesion promoter.

In the above outlined exemplary process, both the perfluorinated alkylsilane and the aminosilane are "radiation reactive materials" which are reactive to radiation that can absorb radiation used to expose them and which undergo a modification as a result of absorption of the radiation. It should be noted that only the first deposited chemical (i.e. that chemical which is deposited in step (b)) needs to be a radiation reactive material (RRM). Preferably, the radiation reactive material (RRM) will absorb light with a wavelength of less than 400 nm. Most preferably the RRM will have an absorption maximum at the wavelength used to expose the material. RRMs include organic, inorganic and polymeric materials. Polymeric materials include polyethers, polyurethanes, polysulfones, polystyrene, polyamides, polymethacrylates, polybutadienes, polyethylene terephthalate, paraffin, polyisoprene and blends and copolymers of such materials. Other materials include chlorosilanes, methoxysilanes, ethoxysilanes, silazanes, titanates, zirconates and the like.

According to the present invention, the process of producing patterned molecular assemblies on a substrate is carried out by providing a substrate having at least one layer of a RRM having substantially equal reactivity over a surface. The surface of the RRM is exposed to patterned radiation to create first and second areas of different reactivity. One additional layer of material may be built directly next to one of said first layer to create a patterned substrate with desired areas of different reactivity.

The invention can comprise a process for producing differential cell-adhesive ultra-thin films (UTFs) on solids by causing a layer or film on the substrate to be altered in its adhesivity. Adherent cells grow and develop only in those regions having a sufficient adhesivity. Preferably, the substrate is of the kind having a polar functional group at its surface and the monomolecular films are self-assembling films which are deposited on the surface of the substrate and can be a monomer or polymer. Yet more preferably, the surface of the self-assembling films are of the type which either promote cell adhesion or inhibit cell adhesion and are capable renewed reactivity upon exposure to deep ultraviolet light (DUV), so that a subsequent self-assembling film can be deposited selectively in the same or similar place as the first self-assembled film, creating patterns of cell adhesion promoters and cell adhesion inhibitors. It is a feature of this invention that patterns of biological cells which can be spaced apart distances of 50–490 µm or less as necessary can be made on a variety of technologically relevant substrates including semiconductors, metals, biocompatable polymers and ceramics.

In a preferable embodiment, cells from established lines or dissociated tissues are plated on patterned substrates in a suitable culture medium. Biological cells only adhere to and develop on those regions of the film that have sufficient adhesivity to bind the cells. After a period of time (e.g. 20 minutes to 2 hours), non-adherent cells are rinsed from the substrate with culture media. When selectively adhered cells are cultured on said substrate in vitro, they develop only in defined substrate regions. A surface exhibits selective adhesion if the surface exhibits an adhesion selectivity of at least 75%, preferably at least 90% and more preferably at least 98%. For the purposes of the present application, the selectivity of cell adhesion for a particular pair of cell adhesion promoter (promoter) and cell adhesion inhibitor (inhibitor) is defined as the percentage of cells adhering to the promoter region out of the total number of cells plated on a surface containing equal areas of the promoter and inhibitor and on which the individual regions of promoter and inhibitor have areas larger than the diameter of the cells being plated.

In another embodiment, either or both of the cell adhesion promoter or inhibitor surfaces may comprise two or more different cell adhesion promotes or inhibitors. Regions containing two or more cell adhesion promoters may be prepared by simply coating with a mixture of compounds containing cell adhesion promoter or inhibitor functional groups. However, because of the lack of stoichiometric control owing to the different rates of reactivity, it is preferred that regions containing two or more promoters or inhibitors be prepared by a process in which the substrate is first coated with a first promoter and the surface is then, either with or without a mask, irradiated with light of suitable wavelength and sufficient intensity to only partially bring about the reaction of the exposed region. In this way, it is possible to remove only a portion of either the promoter or the inhibitor. After the irradiation step, the surface may be treated with another compound to convert the new reactive sites to a second promoter or inhibitor. Thus, by controlling the exposure of the surface to the irradiation (i.e. radiation), it is possible to remove the desired amount of the first promoter or inhibitor in the exposed region and, thus, precisely control the relative amounts of the first and second promoters or inhibitors in the exposed region. Of course, this procedure may be carried out iteratively to prepare regions which contain more than two different promoters or inhibitors.

The generality of the process of forming patterned UTFs of varying cell adhesivity upon substrates that either intrinsically possess, or are treated to have, polar functional groups at the surface has been demonstrated in U.S. patent application Ser. No. 07/182,123 filed on Apr. 14, 1988 and issued into U.S. Pat. No. 5,079,600, and in U.S. patent application Ser. No. 07/022,439 filed on Mar. 6, 1987 and issued into U.S. Pat. No. 5,077,085, each of which are incorporated herein by reference for all purposes in their entirety.

Cell adhesion promoters are attached to the substrate by chemical and physical adsorption which may involve siloxane (Si—O—Si) bridges or Van der Waals forces. Any substrate having a terminal ionizable hydroxyl group at the surface can provide a reactive site for the patterning of cell adhesion promoters and cell adhesion inhibitors. The procedure of using self-assembling UTFs involves covalent bond formation between the monolayer and the substrate whereby the UTF adheres to the substrate more strongly than physisorbed Langmuir-Blodgett films.

The substrate types include, but are not limited to: silica (quartz and glass), silicon (doped and undoped), other semiconductors (e.g. germanium, gallium arsenide), organic polymers such as epoxy resins, polystyrenes, or polysulfones, metals such as aluminum and platinum and metal oxides such as alumina and native or modified biomedically-relevant polymers such as silicones, rubber, fluoropolymers, polyesters, acrylic copolymers, polygalactin, polyacetates, polyactic acids, hydroxyapatite, ceramics and polyglycolic acids.

The details of the formation of the SAM of exemplary EDA molecules, attachment of a photolithographic mask on the UTF (i.e. the SAM of EDA molecules), exposure of the UTF to DUV through the gaps in the mask to form exemplary EDA regions having a desired linewidth and remodification of the DUV exposed regions with exemplary 13F molecules to form a patterned UTF wherein there are adjacent regions of exemplary EDA molecules and regions of exemplary 13F molecules are all described in Stenger D. A., Georger, J. H., Dulcey, C. S., Hickman, J. J., Rudolph, A., Nielsen, T. B., McCort, S. M. and Calvert J. M. in *Coplanar Molecular Assemblies of Amino- and Perfluorinated Alkylsilanes: Characterization and Geometric Definition of Mammalian Cell Adhesion and Growth* published in 14 JACS (No. 22) at pp. 8435-8442 (1992), incorporated by reference for all purposes in its entirety.

Figure 7:
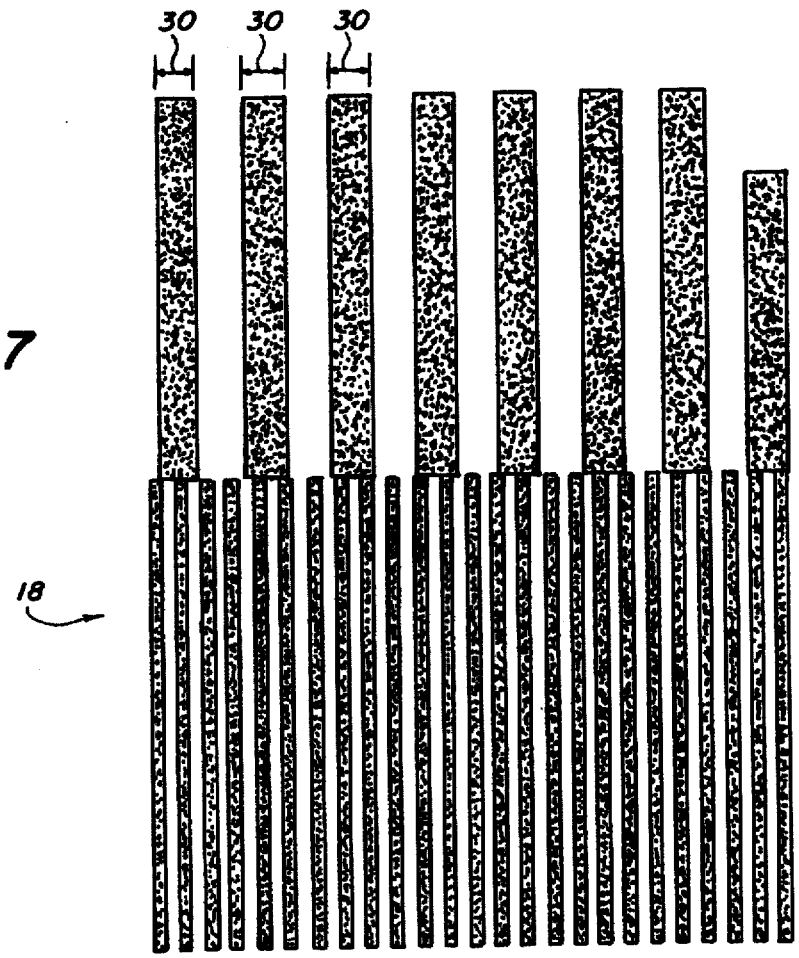
FIG. 7 illustrates a bright field micrograph of the metalized mask used to create the alternating EDA and 13F patterns. Dark regions correspond to the metal used to protect the underlying EDA coated glass substrate. Light regions represent the DUV transparent fused silica substrate of the mask and correspond to regions which are exposed and subsequently remodified with 13F. The interface between two linewidth/line spacing regions is shown. The linewidth 30 corresponds to the DUV opaque (i.e. dark regions of the mask) regions of the photolithographic mask which can be varied as desired. A typical linewidth of between about 50–490 μm is readily achieved.

The linewidths necessary for the formation of longitudinally oriented neo-vascular capillaries are typically between about 50–490 µm, more typically between about 65–400 µm, even more typically between about 70–350 µm, most typically between about 75–300 µm, preferably between about 80–250 µm, more preferably between about 85–200 µm, even more preferably between about 90–150 µm and most preferably between about 95–100 µm. The above linewidths are achieved by using a photolithographic mask, for example as depicted in FIG. 7 wherein the dark regions represent the metalized portions of the photolithographic mask having widths equal to the linewidths of the exemplary EDA regions desired in the UTF pattern formed after irradiation with DUV radiation. Note that the exemplary EDA regions are those regions that promote endothelial cell adhesion and which regions correspond to the pattern of the dark regions of the photolithographic mask depicted in FIG. 7. The wavelength of radiation used to irradiate the EDA coated substrate is typically below 400 nm, and most preferably at 193 nm. However, any wavelength of irradiation can be used that does not obliterate the underlying substrate and simply modifies the exemplary EDA monolayer, as depicted in FIG. 5a, is suitable for use with the presently disclosed invention.

Limitations to resolution in conventional optical lithography arise from the use of relatively thick films (1.0–1.5 µm thick) which suffer from defocussing of the image in the film, the occurrence of standing waves in the film, Rayleigh scattering from film inhomogeneities, and a reduce control of the spatial extent of photoreactions. The present process minimizes these problems through the use of ultra-thin films, which are significantly thinner than a quarter of the wavelength (less than 50 nm) of the light used to expose them. The above mentioned problems are also minimized by using radiation of the shortest possible wavelength to which the resist is sensitive. Most of the currently used high resolution photosensitive materials absorb near UV (i.e. 320 to 400 nm) light. Few known photoresists are useful in the DUV (about 200 to 320 nm) or the vacuum-UV (below about 200 nm) regions. The process disclosed here uses, but is not limited to 193 nm light and is therefore capable of higher resolution than conventional photoresists. Many light sources for UV irradiation are available, including but not limited to mercury lamps, xenon lamps, deuterium lamps, surface plasma discharge sources, Nd-YAG laser, excimer lasers, and optical harmonics generated from other sources.

Referring to FIG. 5a, a substrate, 10, coated with an aminosilane, 16, such as EDA, is covered with a photolithographic mask, 18, which mask is then irradiated with DUV radiation, 20, which results in irradiating only the regions of the aminosilane not photoprotected by the overlying photolithographic mask, 18. The result of the irradiation as depicted in FIG. 5a is shown in FIG. 5b wherein the aminosilane regions, 16, exposed to DUV radiation is modified by the DUV radiation to form regions 22 wherein the previously attached aminosilanes, 16, have been replaced with hydroxyl groups attached to the surface of the substrate, 10. Thereafter, the hydroxyl regions, 22, and the aminosilane regions, 16, are remodified with a perfluorinated alkyl silane, such as 13F, resulting in the formation of regions, 24, coated with 13F as depicted in FIG. 5c. Note that the pattern of regions 22 correspond exactly to the patterned regions 24 formed according to the method described by Stenger et al. in the above-identified JACS article previously incorporated by reference in its entirety.

There are numerous classes of substances whose molecules, under appropriate conditions, self-assemble to form thin films. In general, those self-assembling molecules characteristically include a polar end, a non-polar opposite end with a reactive moiety at or near the terminus and an intermediate region typically composed of saturated or unsaturated hydrocarbon chain or may not have an intermediate region. The spacer can be monomeric or polymeric.

The class of polar end groups (which interact with the polar surface of the substrate) include silanes of the $R_nSiX_m$ type where R is an organic functional group;

n is an integer which is either 1, 2, or 3;

m = 4−n; and

X is a halogen, alkoxy or amino group.

The class of polar end groups further includes carboxylic acids, acid chlorides, anhydrides, sulfonyl groups, phosphoryl groups, hydroxyl groups and amino acid groups.

The class of non-polar end groups include olefins, acetylenes, diacetylenes, acrylates, aromatic hydrocarbons, methacrylates, methyl, perfluorinated hydrocarbons, primary amines, long chain hydrocarbons and esters.

While specific films have been exemplified using specific silanes that either promote or inhibit cell adhesion, many other types of films can be applied to surfaces to control their cell adhesivity. Alternative examples of commercially available aminosilanes that may be used to promote cell adhesion are:

N-(2-aminoethyl-3-aminopropyl)-trimethoxysilane (EDA),
11-aminoundecyltrimethoxysilane,
3-aminopropyltrimethoxysilane,
3-aminopropyltriethoxysilane,
3-aminopropylmethyldiethoxysilane,
3-aminopropyldimethylethoxysilane,
3-(1-aminopropoxy)-3,3-dimethyl-1-propenyltrimethoxysilane,
N-(2-aminoethyl)-3-aminopropylmethyldimethoxysilane,
bis(3-(trimethoxysilyl)propyl)ethylenediamine,
trimethoxysilylpropyldiethylenetriamene and
(aminoethylaminomethyl)phenethyltrimethoxysilane (DAP).

Alternative examples of commercially available fluorosilanes that might be used to inhibit cell adhesion are:

tridecafluoro-(1,1,2,2-tetrahydrooctyl)-1-diemethylchlorosilane (13F),
tridecafluoro-(1,1,2,2-tetrahydrooctyl)-1-methyldichlorosilane,
tridecafluoro-(1,1,2,2-tetrahydrooctyl)-1-triethoxysilane,
(3,3,3-trifluoropropyl)-trichlorosilane,
(3,3,3-trifluoropropyl)-methyldichlorosilane,
(3,3,3-trifluoropropyl)-dimethylchlorosilane,
(3,3,3-trifluoropropyl)-methyldimethoxysilane,
(3,3,3-trifluoropropyl)-trimethoxysilane,
(heptafluoroisopropoxy)-propylmethyldichlorosilane and
(3-pentafluorophenylpropyl)-dimethylchlorosilane (PFP).

Other silanes that have been shown to inhibit cell adhesion such as n-tetradecanetrichlorosilane and N-(3-trimethoxysilyl)-propylethylenediamenetriacetic acid trisodium, along with other long acyl chain chloro-, methoxy, and ethoxy-silanes, may also be used in the same manner as 13F.

In addition, epoxy silanes such as 3-glycidoxypropyltrimethoxysilane may be coated on the substrate surface. Hydrolysis of the epoxide functionality results in formation of a diol which inhibits cell adhesion as discussed in Massia et al, *Anal. Biochem.* Vol. 187, pp. 292–301 (1990) and U.S. Pat. No. 4,562,157, which are each incorporated herein by reference for all purposes in their entirety. Furthermore, the substrate may be coated with a silane containing a terminal olefin, which may then be converted to either an alcohol by hydroboration or a diol by either $KMnO_4$ or $OsO_4$ as described in U.S. Pat. No. 4,539,061, which is incorporated herein by reference for all purposes in its entirety.

Other classes of materials which may act as cell adhesion promoter or inhibitors include titanates. Titanates have the general formula $Ti(OR)_4$, where all four of the OR organic groups may be the same or different. These materials, and the related zirconate and aluminate classes of molecules, are recognized to be similar to silanes in that they spontaneously react with surface hydroxyl groups to give an organic monolayer which is covalently linked to the substrate with the evolution of an alcohol. An O—Ti bond is formed between surface hydroxyls and the titanates. Titanates and zirconates with amino functionalities such as isopropyltri-(n-ethylenediamino)-ethyltitanate, neopentyl-(dialiyl)-oxytri-(n-ethylenediamino)-ethyltitanate, neopentyl-(dialiyl)-oxytri-(n-amino)-phenyltitanate, neopentyl-(dialiyl)-oxytri-(n-ethylenediamino)-ethylzirconate and neopentyl-(dialiyl)-oxytri-(n-amino)-phenylzirconate may be used to promote cell adhesion.

Potential cell adhesion inhibitors for cells include titanates and zirconates where long fluorinated or unfluorinated alkyl chains are present in the molecule. Other SAM film forming materials that may be used to control cell adhesion include thiol or disulfide films that assemble on gold surfaces and carboxylic acids or acid chlorides that assemble on surfaces such as alumina and other meta oxides. A preferred cell adhesion inhibitor is one which contains one or more fluorinated alkyl groups.

Alternative strategies for creating differential cell adhesive patterns may also involve the covalent attachment of cell adherent biological moieties to preformed UTF patterns. For example, covalently binding cell adhesive peptides such as GLY-ARG-GLY-ASP-TYR (SEQ ID NO:1) and GLY-TYR-ILE-GLY-SER-ARG-TYR (SEQ ID NO:2) to glass surfaces may be used in conjunction with a modification of the disclosed process described here. This modification involves the treatment of a surface with an adhesion inhibitor such as 13F, irradiation to form a pattern of regions devoid of the cell adhesion inhibitor and treating the surface with a glycerolpropylsilane, such as 3-glycidoxypropyltrimethoxysilane to bind to the region devoid of cell adhesion inhibitor. The attached glyceropropylsilane may then be modified as described in Massia et al. *Anal Biochem.* Vol. 187, p. 292 (1990), incorporated herein by reference for all purposes in its entirety, creating a surface that will selectively adhere various cell types. The patterning technique allows sequential modification with more than two chemical functionalities. Thus, cell-specific adhesive patterns might be designed.

Although it is not possible to pattern many of the cell adhesion inhibitors mentioned above with 193 nm or longer wavelength light, it has been demonstrated in U.S. patent application Ser. No. 07/182123 (U.S. Pat. No. 5,079,600) that these films can be patterned with shorter wavelength light, such as the 185 nm light from a low pressure mercury argon pen lamp or with even shorter wavelengths. It should be noted that several of the above-mentioned molecular species, such as DAP and PFP, are phenyl derivatives which will absorb at wavelengths longer than 193 nm and may be patterned at longer wavelengths as described in U.S. patent application Ser. No. 07/182123 (U.S. Pat. No. 5,079,600).

Figure 6:
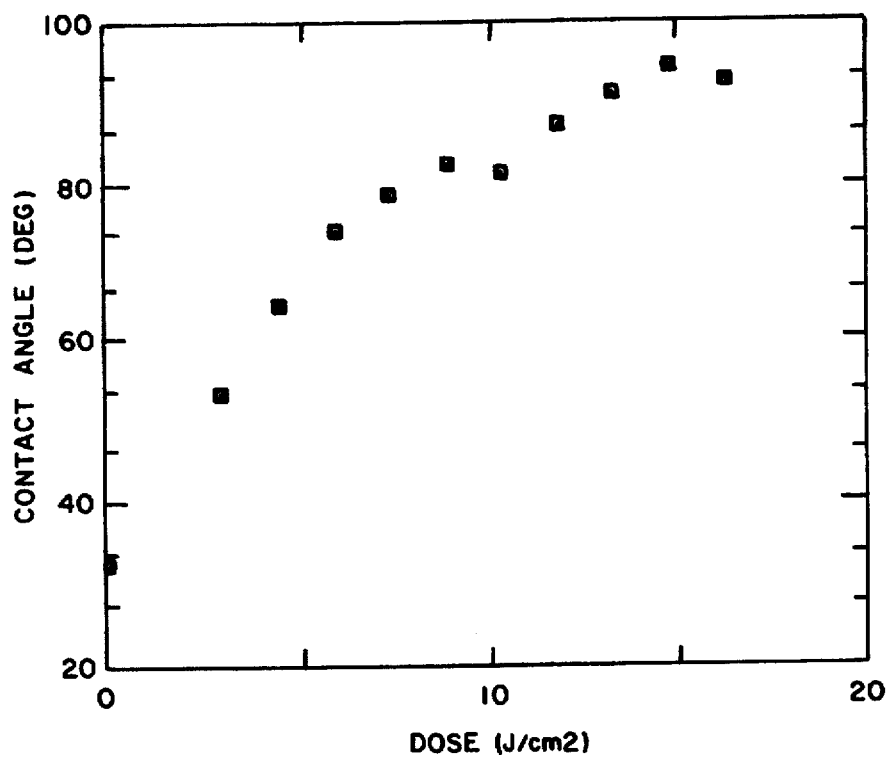
FIG. 6 illustrates the change in the contact angle of EDA coated glass (i.e. such as depicted in FIG. 5a) following exposure to increased amounts of DUV energy and subsequent modification with 13F. Individual 1 $cm^2$ areas of EDA UTFs on glass microscope slides were exposed to 193 nm DUV from a pulsed argon fluoride excimer laser (10 Hz at 10–20 mJ/$cm^2$ per pulse), then exposed to a 1% solution of 13F in toluene. The water contact angle (as measured using the sessile drop method) of the remodified areas increased from that corresponding to a pure EDA UTF (i.e. 28–32 degrees) to that of pure 13F UTF (i.e. 92–96 degrees) as the exposure was increased from 0 to 15 J/$cm^2$.

The relationship between the dose of the DUV radiation, 20, versus the contact angle is depicted in FIG. 6. The presence of a aminosilane on the surface of the substrate 10 is denoted by a contact angle of between 28–32 degrees and the presence of 13F regions is denoted by a contact angle of between 92–96 degrees as determined by the Advancing Water Drop Method. From FIG. 6, it is apparent that an irradiation dose of 15 $J/cm^2$ is preferred in order to form regions 22 as depicted in FIG. 5b which regions 22 are completely free of aminosilanes 16.

Figure 4:
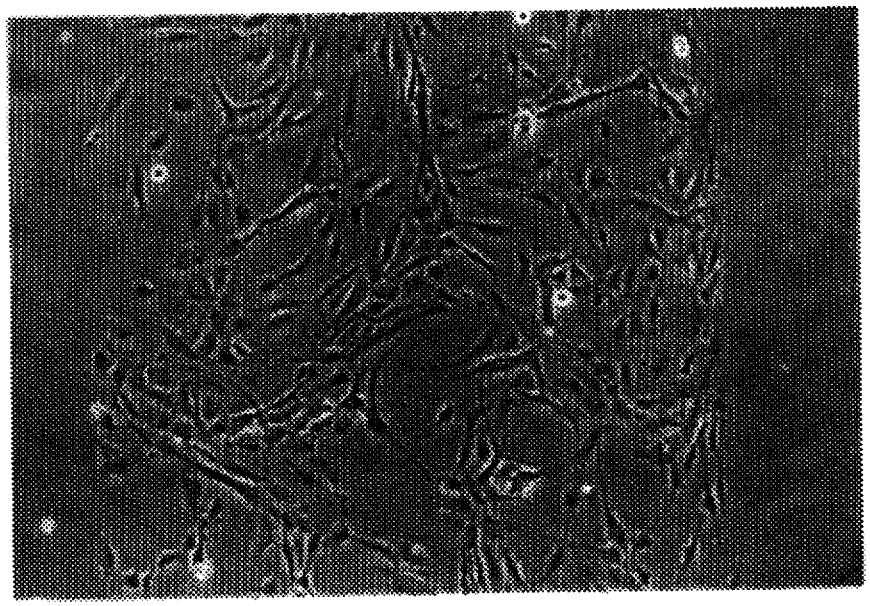
FIG. 4 is a photograph of endothelial cell that were adhered, grown, differentiated and photographed 5 days after seeding. The cells were seeded onto a patterned UTF attached to a glass substrate. The initial endothelial seeding cell density at time=0 days was 10,000 cells/cm$^2$. B-FGF was added at time=4 days after seeding when confluency was reached to promote cell differentiation at a concentration of 5 ng/ml. The underlying UTF linewidth of the EDA region was 500 μm. Note that while growth and differentiation into neo-vascular capillary formation is obtained and while the b-FGF was added at confluency, the neo-vascular capillaries formed do not longitudinally orient themselves along a single longitudinal axis of the capillaries formed as is visible in FIG. 3. The lack of longitudinal orientation is because the linewidth=500 μm of the EDA region is too large for the formation of the desired longitudinally oriented neo-vascular capillaries. The cells are labelled as sample MT 625 for convenience.

Note that the linewidth of the aminosilane regions 16 (i.e. substrate 10 coated with, for example, EDA) is depicted as 30 in FIG. 5c. It is critical that the linewidth 30 of the cell adhesion promoting regions 16 have the proper dimensions to later allow the formation of longitudinally oriented neo-vascular capillaries. Referring to FIG. 4, wherein the linewidth of the underlying EDA region was 500 µm, it is apparent that while neo-vascular capillaries are formed, the capillaries are not longitudinally oriented and, therefore, are of little utility in the further development of predictable spatially oriented vasculature formation. Similarly, a linewidth of 100 µm, as depicted in FIG. 3 on the left as marked, is also not suitable for complete longitudinal orientation of the neo-vascular capillaries formed. Compare the incomplete longitudinal orientation of the left side of FIG. 3 to the complete longitudinal orientation of the right side of FIG. 3. The only difference between the left and the right side as marked in FIG. 3 is that the linewidths are 100 µm and 50 µm, respectively. Thus, the criticality of having a proper linewidth is born out by the exemplary experimental results depicted in FIGS. 3 and 4.

Another critical feature leading to the successful formation of longitudinally oriented neo-vascular capillary formation is the seeding density used. Typically the seeding density is between about 2,500–10,000 cells/$cm^2$. More typically the seeding density is between about 5,000–10,000 cells/$cm^2$. Most typically the seeding density is 10,000 cells/$cm^2$.

Another critical feature leading to the successful formation of longitudinally oriented neo-vascular capillary formation is the time to confluency. The time to confluency is the minimum amount of time necessary for the growth of the seeded endothelial cells to coat nearly completely the linewidth of the aminosilane coated cell adhesion promoting regions. Typically, the time to confluency is between 1–20 days. However, note that with a lower seeding density such as 2,500 cells/$cm^2$ and a larger linewidth such as 490 µm, the time to confluency may be longer than the typical time to confluency. Conversely, note that with higher seeding density such as 10,000 cells/$cm^2$ and a smaller linewidth such as 50 µm, the time to confluency may be shorter than the typical time to confluency. More typically, the time to confluency is between 1–10 days. Even more typically, the time to confluency is between 1–8 days. Most typically, the time to confluency is between 1–7 days. Preferably, the time to confluency is between 1–6 days. More preferably, the time to confluency is between 1–5 days. Most preferably, the time to confluency is between 2–5 days.

The seeded endothelial cells are grown in a first medium such as M-199 containing up to 2% (v/v) fetal bovine serum, 10 ng/ml endothelial cell growth factor (ECGF) and bovine brain extract (BBE) among other components. It is critical to add the ECGF to cause the endothelial cells to be able to grow to confluency. Further the presence of fetal bovine serum or other suitable serum medium is necessary for the growth to confluency to be successfully accomplished. Note that the first medium is replaced every other day for the during the time to confluency. Further note that when the seeded cells are HUVECs, ECGF and BBE are present in the first medium. When the seeded cells are PCMVECs, retinal extract is present in the first medium instead of ECGF and BBE. In the case of HUVECs, after confluency is reached, ECGF and BBE are removed from the first medium and b-FGF is added by replacing the first medium with a second medium. Likewise, in the case of PCMVECs, after confluency is reached, retinal extract is removed from the first medium and b-FGF is added by replacing the first medium with a second medium. The composition of the first medium without the presence of ECGF and BBE and the addition of b-FGF is referred to as the second medium, in the case of HUVECs. The composition of the first medium without the presence of retinal extract and the addition of b-FGF is referred to as the second medium, in the case of PCMVECs. At confluency, the first medium is replaced with the second medium to promote cell differentiation into neo-vascular capillaries. Typically, confluency is reached at 1–4 days post seeding. More typically, confluency is reached at 1–3 days post seeding. Even more typically, confluency is reached 1–2 days post seeding. Most typically, confluency is reached 1 day post seeding. However, it should be noted that with a high initial seeding cell density (e.g. 10,000 cells/cm$^2$) and a small linewidth (e.g. 50 μm) confluency may be reached sooner than the most typical time (i.e. 1 day) to confluency cited above. Conversely, with a low initial seeding cell density (e.g. 2,500 cells/cm$^2$) and a high linewidth (e.g. 490 μm) confluency may be reached later than the typical time (i.e. 1–4 days) to confluency cited above.

The exact composition of M-199 is given in the following references, each of which is incorporated herein by reference in its entirety:

Morgan, J. F., et al., Nutrition of animal cells in tissue culture I. Initial studies on a synthetic medium. Proc. Soc. Exp. Biol. Meal. 73:1–8, 1950; Morton, H. J. A survey of commercially available tissue culture media. In Vitro 6:89–108, 1970; and Rutzky, L. P. and R. W. Pumper. Supplement to a survey of commercially available tissue culture media (1970). In Vitro 9: 468–469, 1974. M-199 consists substantially of the following components in the following concentrations. Essential amino acids: arginine (3.3E-4), cysteine (6.3E-7), half-cysteine (1.7E-4), glutamine (6.8E-4), histidine (1.0E-4), isoleucine (3.0E-leucine (9.1E-4), lysine (3.8E-4), methionine (2.0E-4), phenylalanine (3.0E-4), threonine (5.0E-4), tryptophan (2.2E-4), tyrosine (2.2E-4), valine (4.3E-4). Nonessential amino acids: alanine (5.6E-4), aspartate (4.5E-4), glutamate (9.1E-4), glycine (6.7E-4), proline (3.5E-4), serine (4.8E-4). Amino acid derivatives: α-amino butyrate (3.6E-7), glutathiophone (1.6E-7), hydroxy-proline (7.6E-5). Water soluble vitamins and co-enzymes: ascorbic acid (2.8E-7), biotin (4.1E-8), folio acid (2.3E-8), p-amino benzoic acid (3.6E-7), nicotinic acid (2.0E-7), nicotinamide (2.0E-7), pantothenic acid (4.2E-6), pyridoxine (1.2E-7), pyridoxal (1.2E-7), riboflavin (2.7E-8), thiamine (3.0E-8). Fat soluble vitamins: vitamin D (2.5E-7), vitamin K (5.8E-8), vitamin E (2.0E-8), vitamin A (3.5E-7). Carbohydrates and their derivatives: acetate (6.1E-4), deoxyribose (3.7E-6), glucose (5.6E-3), ribose (3.3E-6). Nucleic acid derivatives (purine): arenine (3.3E-6), AMP (5.8E-7), ATP (1.8E-6), guanine (1.6E-6), hypoxanthine (2.2E-6), xanthine (2.0E-6). Nucleic acid derivatives (pyrimidine): thymine (2.4E-6), uracil (2.7E-6). Lipids and their derivatives: cholesterol (5.2E-7), choline (3.6E-6), i-inositol (2.8E-7). Bulk inorganic ions: calcium (1.8E-3), magnesium (8.1E-4), potassium (5.4E-3), sodium (1.5E-1), chloride (1.3E-1), nitrate (1.2E-6), phosphate (1.0E-3), sulfate (8.6E-4). Inorganic trace elements: iron (4.1E-7). Buffers and indicators: bicarbonate (2.6E-2), carbon dioxide gas (8%), phenol red (4.2E-5). Chelating agents and solvents: Tween 80 (20.0 mg/1000 ml). The notation 'E-x' denotes $10^{-x}$ moles/liter.

It is critical that the b-FGF be introduced with the second medium when confluency is reached. Introduction of b-FGF causes inhibition of proliferation of the endothelial cells that have reached confluency and induces these endothelial cells to differentiate.

Several types of biological cells that are susceptible to the presently disclosed inventive process are HUVECs, PCMVECs, primary micro-vascular endothelial cells, primary vascular endothelial cells and transformed cells of endothelial origin.

Other features of the invention will become apparent in the course of the following descriptions of exemplary embodiments which are given for illustration of the invention and not intended to be limiting thereof.

EXAMPLES

Example 1

Chemicals:

EDA and 13F were used as received from Huls of America, Petrarch Silanes. Anhydrous (<0.005% H$_2$O) methanol and toluene were obtained from Aldrich. Other reagents used were chloroform (Baker; 0.75% EtOH), acetonitrile (Baxter Healthcare), and hexane (Fisher Scientific). All silane reagents were opened, stored, and dispensed under a dry (<1 ppm H$_2$O) helium atmosphere. All water was deionized to ≧17.6 MΩ/cm resistance. Two model amine compounds, tert-butylamine, (t-Bu)NH$_2$, and dibutylamine, (n-Bu)$_2$NH, were obtained from Aldrich.

Example 2

SAM Formation:

The 3"×1" glass microscope slides (Fisher Scientific), 1"×1" fused silica slides (Dell Optics), and 50-mm diameter <100> n-type silicon wafer (Recticon) substrates were cleaned by immersion in 1:1 methanol/HCl for at least 30 minutes at room temperature, rinsing thoroughly in water and immersion in concentrated H$_2$SO$_4$ for at least 30 minutes. Platinum surfaces were prepared by resistive evaporation of platinum onto silicon wafers and oxidized using the H$_2$SO$_4$ treatment. All cleaned substrates were transferred to boiling water for 10–15 minutes prior to reaction with silanes. EDA SAMs were formed by immersing cleaned substrates in freshly mixed 94% acidic methanol (1.0 mM acetic acid in methanol), 5.0% H$_2$O, and 1.0% EDA for 15 minutes at room temperature and then rinsing three times in methanol. All percentages were in v/v. 13F SAMs were formed by immersing clean or irradiated (vide infra) EDA substrates in a solution of 1.0–2.0% 13F in either toluene, hexane, chloroform, or acetonitrile for 0.5–3.0 hours at room temperature and then rinsing three times with the same solvent. Following the final rinse step in both the EDA and 13F preparations, slides were baked on a hotplate at 120 degrees Centigrade for 5 minutes. The baking step was performed to quickly remove residual solvent and promote the complete reaction of the silanes. All SAM formation steps were performed in a class 100 clean room or in a Vacuum Atmospheres drybox with a helium atmosphere.

The quality of the EDA SAMs was sometimes observed to be dependent on the duration of time between the mixture of EDA with acidic methanol and the addition of water. Delays of more than 20 minutes led to nonuniform surface coverage and partial polymerization of EDA in solution prior to deposition. These phenomena were evidenced by large variation in the advancing water contact angle measurements across a substrate surface and visible bulk film formation, respectively. In all cases reported here, water was added to the EDA/methanol mixture within 3 minutes and the reaction with substrates was initiated immediately pendent of the reagent mixing and reaction times. 13F SAMs exhibited nearly identical properties for reaction times of 30 minutes and 3.0 hours. The same was true both of 13F films formed on native substrates and on irradiated EDA-treated substrates that were exposed to >10J/cm$^2$.

Example 3

Deep Ultraviolet Irradiation and Pattern Formation:

Individual 3 cm$^2$ areas of EDA-treated surfaces were exposed to 193 nm deep UV radiation using a Questek Model 2430 ArF excimer laser. Deep UV pulses, having single shot power densities of 100–600 kW/cm$^2$, were delivered at a 30-Hz repetition rate. Patterned exposures were performed by positioning the EDA-treated surfaces of the substrates tightly against the metalized surface of a fused silica photolithographic mask. A 3"×3" fused silica mask was used, which had the desired geometrical features defined by a pattern of metal (chrome) on one surface. The metal features on the mask protected regions of the EDA from exposure to the deep UV irradiation. Immediately following the exposures, the substrates were immersed in a 1.0–2.0% (v/v) mixture of 13F in toluene, in an attempt to selectively remodify the exposed regions. The overall pattern forming process is shown in FIGS. 5a, 5b and 5c. Mixed films of EDA and 13F were formed in the same way except that the EDA-treated substrates were exposed to intermediate levels (1–15J/cm$^2$) of unpatterned 193 nm radiation (no lithographic mask used).

Example 4

Cell Culture:

Prior to cell plating, the patterned substrates were sterilized by immersion in 70% of pure ethanol for 30 minutes. Porcine aortic endothelial cells were isolated, established in culture as described in Robinson, D. H.; Kang, Y. H.; Deschner, S. H.; Nielsen, T. B. *In Vitro Cell Dev. Biol.* Vol. 26, pp. 169–180 (1990), incorporated herein by reference in its entirety and for all purposes, and seeded onto EDA/13F patterns.

Example 5

PGA Preparation:

PGA surfaces were prepared for chemical modification by heat annealing and/or hydrolysis. PGA wafers were annealed by incubating the wafers at 100° C., 1 Atm. for 24 h. PGA wafers were hydrolyzed using a potassium phosphate buffer consisting of a 1:4 (v/v) mixture of 3.484% (w/v) monobasic and 2.72% (w/v) dibasic potassium phosphate. The pH of the final potassium phosphate buffer was adjusted to 7.44. PGA in the form a wafer discs are hydrolysed from 4–24 h at 37° C. After hydrolysis, the discs were rinsed in cell culture phosphate buffered saline several times and air-dried. Prior to modification of the surface with N-2-aminoethyl-3-aminopropyl-trimethoxysilane (EDA), the discs were rinsed 3–4 times in hexanes and air-dried. EDA at 1% (v/v) in methanol containing 1 mM acetic acid was used as the reaction medium as described by Dulcey et al (Science vol. 252, 551, 1991) using silica.

Endothelial Cell Seeding:

Endothelial cells are seeded on the PGA surface between 2500 and 10,000 cells/cm$^2$. Cells are incubated in medium M-199 containing up to 2% (v/v) fetal bovine serum, 10 ng/ml endothelial cell growth factor (ECGF), 1 µg/ml hydrocortisone, and up to 0.4% (v/v) bovine brain extract (BBE) at 37° C., 5% CO$_2$ in air. Cells are grown to confluency on the substrate. At confluency, cells are differentiated by the addition of basic fibroblast growth factor at 10 ng/ml and the elimination of ECGF and BBE from the medium. Under all conditions, medium is replaced every other day.

Example 6

Deposition of EDA and 13F on solid substrates such as glass and metal is accomplished using the photolithography method of Dulcey et. al (1991). Substrates are washed in methanol:HCl (1:1 v/v) for 1 h. and 18M H$_2$SO$_4$ for 1 h followed by multiple washes with deionized water (18 MΩ). Final wash consisted of immersion of the substrate in boiling deionized water immediately followed by deposition of EDA using a 1% solution of the aminosilane in 95% aqueous methanol containing 1 mM acetic acid. After a 20 min incubation in EDA, substrates are removed, rinsed in anhydrous methanol and baked at 120° C. for 5 min. 13F is deposited using a 1% (v/v) solution of the silane in anhydrous toluene. Deposition of 13F is under anhydrous conditions by incubation for 45 min followed by an anhydrous toluene rinse and baking at 120° C. for 5 min.

Coplanar two-component SAM films of EDA and 13F were generated according to the method of Dulcey et al. (1991). Briefly, an EDA film was exposed to 193-nm radiation (≈13 J cm$^{-2}$) through a lithographic mask. Photoablated regions of the substrate were resilanized with 13F as described above.

Cell seeding and differentiation are done as described in EXAMPLE 5.

Example 7

Substrates are prepared as described in EXAMPLE 6. Some substrates were further modified by the adsorption of hFN or HS. Substrates were incubated at 4° C. in a sterile PBS solution containing hFN (200 ng/ml) or HS (100 µg/ml) for 24 h.

Cell seeding and differentiation are done as described in EXAMPLE 5.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( C ) STRANDEDNESS: Not Applicable
      ( D ) TOPOLOGY: linear ( i i ) MOLECULE TYPE: protein ( i i i ) HYPOTHETICAL: no ( i v ) ANTI-SENSE: no ( x i ) SEQUENCE DESCRIPTION: SEQ ID NO: 1:

```
GLY  ARG  GLY  ASP  TYR
 1                   5
```

( 2 ) INFORMATION FOR SEQ ID NO:2:

( i ) SEQUENCE CHARACTERISTICS:
      ( A ) LENGTH: 7 amino acids
      ( B ) TYPE: amino acid
      ( C ) STRANDEDNESS: Not Applicable
      ( D ) TOPOLOGY: linear ( i i ) MOLECULE TYPE: protein ( i i i ) HYPOTHETICAL: no ( i v ) ANTI-SENSE: no ( x i ) SEQUENCE DESCRIPTION: SEQ ID NO: 2:

```
GLY  TYR  ILE  GLY  SER  ARG  TYR
 1                   5
```

What is claimed is:

1. A process for forming longitudinally oriented neo-vascular capillaries, said process comprising the steps of:

(a) providing a combination ultra-thin film (UTF) pattern of at least one cell adhesion promoter and at least one cell adhesion inhibitor wherein said cell adhesion promoters have a linewidth of between about 50–490 µm;

(b) seeding said combination UTF pattern with cells capable of forming capillaries at an initial seeding cell density;

(c) adding a first medium for incubating said seeded cells until said cells are grown to confluency, wherein said first medium is a medium for promoting cell growth;

(d) replacing said first medium with a second medium at confluency, wherein said second medium is a medium for promoting cell differentiation; and (e) allowing said cells to differentiate into spatially oriented neo-vascular capillaries oriented parallel to said UTF pattern of said at least one cell adhesion promoter.

2. The process of claim 1 wherein said step (a) of providing further comprises:

(f) coating a substrate having a first exposed surface with a compound to obtain an ultra-thin film (UTF) which is reactive to radiation and has a second exposed surface of at least one cell adhesion promoter or cell adhesion inhibitor;

(g) irradiating said second exposed surface of said UTF in a pattern having one or more lines having linewidths between about 50–490 µm to obtain an irradiated film in which a fraction of said cell adhesion promoters or said cell adhesion inhibitors have been removed to reexpose said first exposed surface; and (h) treating said irradiated film with a second compound to bind to said reexposed surface in which at least a fraction of said cell adhesion promoter or cell adhesion inhibitor has been removed to form said combination UTF pattern.

3. The process of claim 2, wherein said cell adhesion promoter is selected from the group consisting of:

N-(2-aminoethyl-3-aminopropyl)-trimethoxysilane (EDA), 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, N-(2-aminoethyl)-3-aminopropylmethyldimethoxysilane, bis(3-(trimethoxysilyl)propyl)ethylenediamine, trimethoxysilylpropyldiethylenetriamene, (aminoethylaminomethyl)phenethyltrimethoxysilane (DAP), isopropyltri-(n-ethyledenediamino)-ethyltitanate, neopentyl-(dialiyl)-oxytri-(n-ethylenediamino)-ethyltitanate, neopentyl-(dialiyl)-oxytri-(n-amino)-phenyltitanate, neopentyl-(dialiyl)-oxytri-(n-ethylenediamino)-ethylzirconate, neopentyl-(dialiyl)-oxytri-(n-amino)-phenylzirconate, a peptide of the sequence GLY-ARG-GLY-ASP-TYR (SEQ ID NO:1), and a peptide of the sequence GLY-TYR-ILE-GLY-SER-ARG-TYR (SEQ ID NO:2) and mixtures thereof;

wherein said cell adhesion inhibitor is selected from the group consisting of:

tridecafluoro-(1,1,2,2-tetrahydrooctyl)-1-diemethylchlorosilane (13F), tridecafluoro-(1,1,2,2-tetrahydrooctyl)-1-methyldichlorosilane, tridecafluoro-(1,1,2,2-tetrahydrooctyl)-1-triethoxysilane, (3,3,3-trifluoropropyl)-trichlorosilane, (3,3,3-trifluoropropyl)-methyldichlorosilane, (3,3,3-trifluoropropyl)-dimethylchlorosilane, (3,3,3-trifluoropropyl)-methyldimethoxysilane, (3,3,3-trifluoropropyl)-trimethoxysilane, (heptafluoroisopropoxy)-propylmethyldichlorosilane, (3-pentafluorophenylpropyl)-dimethylchlorosialne (PFP), 3-glycidoxypropyltrimethoxysilane, and mixtures thereof;

wherein said substrate is selected from the group consisting of:

quartz silica,
glass silica,
silicon,
germanium,
gallium arsenide,
epoxy resins,
polysytrenes,
polysulfones,
aluminum,
platinum,
alumina,
silicones,
rubber,
fluoropolymers,
polyesters,
acrylic copolymers,
polygalactin,
polyacetates,
polyglycolic acids,
polylactic acids,
hydroxyapatite,
ceramics,
and mixtures thereof; and
wherein said cells are HUVECs.

4. The process of claim 3, wherein said first medium further comprises M-199, serum, ECGF and BBE; wherein said first medium is replaced with fresh first medium at least every other day; wherein said second medium further comprises M-199, serum and b-FGF and does not contain ECGF and does not contain BBE; and wherein said second medium is replaced with fresh second medium at least every other day.

5. The process of claim 4, wherein said linewidth of said cell adhesion promoters is between about 65–40.0 µm.

6. The process of claim 5, wherein said linewidth of said cell adhesion promoters is between about 70–350 µm.

7. The process of claim 6, wherein said linewidth of said cell adhesion promoters is between about 75–300 µm.

8. The process of claim 7, wherein said linewidth of said cell adhesion promoters is between about 80–250 µm.

9. The process of claim 8, wherein said linewidth of said cell adhesion promoters is between about 85–200 µm.

10. The process of claim 9, wherein said linewidth of said cell adhesion promoters is between about 90–150 µm.

11. The process of claim 10, wherein said linewidth of said cell adhesion promoters is between about 95–100 µm.

12. The process of claim 2, wherein said cell adhesion promoter is selected from the group consisting of:

N-(2-aminoethyl-3-aminopropyl)-trimethoxysilane (EDA), 11-aminoundecyltrimethoxysilane, 3-aminopropyltrimethoxysilane, 3-aminopropyltriethoxysilane, 3-aminopropylmethyldiethoxysilane, 3-aminopropyldimethylethoxysilane, 3-(1-aminopropoxy)-3,3-dimethyl-1-propenyltrimethoxysilane, N-(2-aminoethyl)-3-aminopropylmethyldimethoxysilane, bis(3-(trimethoxysilyl)propyl)ethylenediamine, trimethoxysilylpropyldiethylene-triamene, (aminoethylaminomethyl)phenethyltrimethoxysilane (DAP), isopropyltri-(n-ethylenediamino)-ethyltitanate, neopentyl-(dialiyl)-oxytri-(n-ethylenediamino)-ethyltitanate, neopentyl-(dialiyl)-oxytri-(n-amino)-phenyltitanate, neopentyl-(dialiyl)-oxytri-(n-ethylenediamino)-ethylzirconate, neopentyl-(dialiyl)-oxytri-(n-amino)-phenylzirconate, a peptide of the sequence GLY-ARG-GLY-ASP-TYR (SEQ ID NO:1), and a peptide of the sequence GLY-TYR-ILE-GLY-SER-ARG-TYR (SEQ ID NO:2) and mixtures thereof;

wherein said cell adhesion inhibitor is selected from the group consisting of:

tridecafluoro-(1,1,2,2-tetrahydrooctyl)-1-diemethylchlorosilane (13F), tridecafluoro-(1,1,2,2-tetrahydrooctyl)-1-methyldichlorosilane, tridecafluoro-(1,1,2,2-tetrahydrooctyl)-1-triethoxysilane, (3,3,3-trifluoropropyl)-trichlorosilane, (3,3,3-trifluoropropyl)-methyldichlorosilane, (3,3,3-trifluoropropyl)-dimethylchlorosilane, (3,3,3-trifluoropropyl)-methyldimethoxysilane, (3,3,3-trifluoropropyl)-trimethoxysilane, (heptafluoroisopropoxy)-propylmethyldichlorosilane, (3-pentafluorophenylpropyl)-dimethylchlorosialne (PFP), 3-glycidoxypropyltrimethoxysilane, and mixtures thereof;

wherein said substrate is selected from the group consisting of:

quartz silica,
glass silica,
silicon, germanium,
gallium arsenide,
epoxy resins,
polysytrenes,
polysulfones,
aluminum,
platinum,
alumina,
silicones,
rubber,
fluoropolymers,
polyesters,
acrylic copolymers,
polygalactin,
polyacetates,
polyglycolic acids,
polylactic acids,
hydroxyapatite,
ceramics,
and mixtures thereof; and
wherein said cells are PCMVECs.

13. The process of claim 12, wherein said first medium further comprises M-199, serum, and BBE; wherein said first medium is replaced with fresh first medium at least every other day; wherein said second medium further comprises M-199, serum and does not contain retinal extract; and wherein said second medium is replaced with fresh second medium at least every other day.

14. The process of claim 13, wherein said linewidth of said cell adhesion promoters is between about 65–400 µm.

15. The process of claim 14, wherein said linewidth of said cell adhesion promoters is between about 70–350 µm.

16. The process of claim 15, wherein said linewidth of said cell adhesion promoters is between about 75–300 µm.

17. The process of claim 16, wherein said linewidth of said cell adhesion promoters is between about 80–250 µm.

18. The process of claim 17, wherein said linewidth of said cell adhesion promoters is between about 85–200 µm.

19. The process of claim 18, wherein said linewidth of said cell adhesion promoters is between about 90–150 µm.

20. The process of claim 19, wherein said linewidth of said cell adhesion promoters is between about 95–100 µm.

21. The process of claim 1 wherein said cell adhesion promoter is an aminosilane; and wherein said cell adhesion inhibitor is a fluorosilane.

22. The process of claim 1 wherein said cells are selected from the group consisting of primary micro-vascular endothelial cells, primary vascular endothelial cells, transformed cells of endothelial origin and mixtures thereof.

23. The process of claim 1, wherein said first medium contains a cell growth agent and is essentially free of cell differentiation agent, and wherein said second medium contains cell differentiation agent.

24. The process of claim 1, wherein said cells are endothelial cells.

* * * * *